United States Patent [19]
Toida

[11] Patent Number: 5,428,447
[45] Date of Patent: Jun. 27, 1995

[54] METHOD AND APPARATUS FOR OBTAINING THREE-DIMENSIONAL INFORMATION OF SAMPLES USING COMPUTER TOMOGRAPHY

[75] Inventor: Masahiro Toida, Kanagawa, Japan

[73] Assignee: Fuji Photo Film Co., Ltd., Kanagawa, Japan

[21] Appl. No.: 100,365

[22] Filed: Aug. 2, 1993

[30] Foreign Application Priority Data

| Jul. 31, 1992 | [JP] | Japan | 4-205306 |
| Jul. 31, 1992 | [JP] | Japan | 4-205307 |
| Jul. 31, 1992 | [JP] | Japan | 4-205308 |
| Jul. 31, 1992 | [JP] | Japan | 4-205309 |
| Jul. 31, 1992 | [JP] | Japan | 4-205310 |

[51] Int. Cl.$^6$ .......................................... G01N 21/27
[52] U.S. Cl. ..................... 356/372; 356/349; 356/432
[58] Field of Search ............. 356/372, 432, 349, 360; 128/633

[56] References Cited

U.S. PATENT DOCUMENTS 4,386,854  6/1983  Byer ........................... 356/438

FOREIGN PATENT DOCUMENTS 0445293  9/1991  European Pat. Off. .
0449597  10/1991  European Pat. Off. .
0458601  11/1991  European Pat. Off. .
WO880148  3/1988  WIPO .

OTHER PUBLICATIONS

"Three-Dimensional Helical-Scan Computer Tomography Using Cone-Beam Projections" in Symposium of the Institute of Electronics and Communication Engineers of Japan, D-III, vol. J75-D-II, 1708, 8 Aug. 1991.
"Optical CT Microscope and Three-Dimensional Observation" Optical Technology Contact vol. 28, No. 11, 1990.
Applied Optics, vol. 31, No. 5, Feb. 10, 1992, pp. 670–674, Noda et al.: "Three Dimensional Phase Contrast, Etc.".
Applied Optics, vol. 30, No. 28, Oct. 1, 1991, pp. 4148–4153, Milbocker et al.: "Comparison Of Three Dimensional Retinal Imaging, Etc."
Electronics & Communications In Japan II: Electronics, vol. 75, No. 4, Apr. 1, 1992, New York, pp. 1–16 XP312129, Toida et al.: "Optical Computed Tomograph, Etc."
Applied Optics, vol. 23, No. 16, Aug. 15, 1984, pp. 2678–2685, Bennett et al.: "Experimental Optical Fan Beam Tomography".
Optics Letters, vol. 16, No. 16, Aug. 15, 1991, pp. 1280–1282, Beiting: "Fast Optical Absorption Tomography."

*Primary Examiner*—Richard A. Rosenberger
*Attorney, Agent, or Firm*—Sughrue, Mion, Zinn, Macpeak & Seas

[57] ABSTRACT

A laser beam, which has been formed into the shape of a conical beam, is irradiated to a sample and is displaced with respect to the sample such that the laser beam may helically scan the sample. The laser beam having passed through the sample to the same direction as the direction, along which the laser beam impinging upon the sample propagates conically, is selected from the laser beam, which has scanned the sample and which has been radiated out of the sample, by using an image forming lens and a pinhole. A two-dimensional intensity distribution of the laser beam, which has passed through the sample and which has been selected, is detected. Three-dimensional information representing the form and/or structure of the sample is then obtained from the detected two-dimensional intensity distribution by using a computed tomography technique. Three-dimensional information of a sample containing a light scattering medium is thereby obtained accurately.

38 Claims, 17 Drawing Sheets

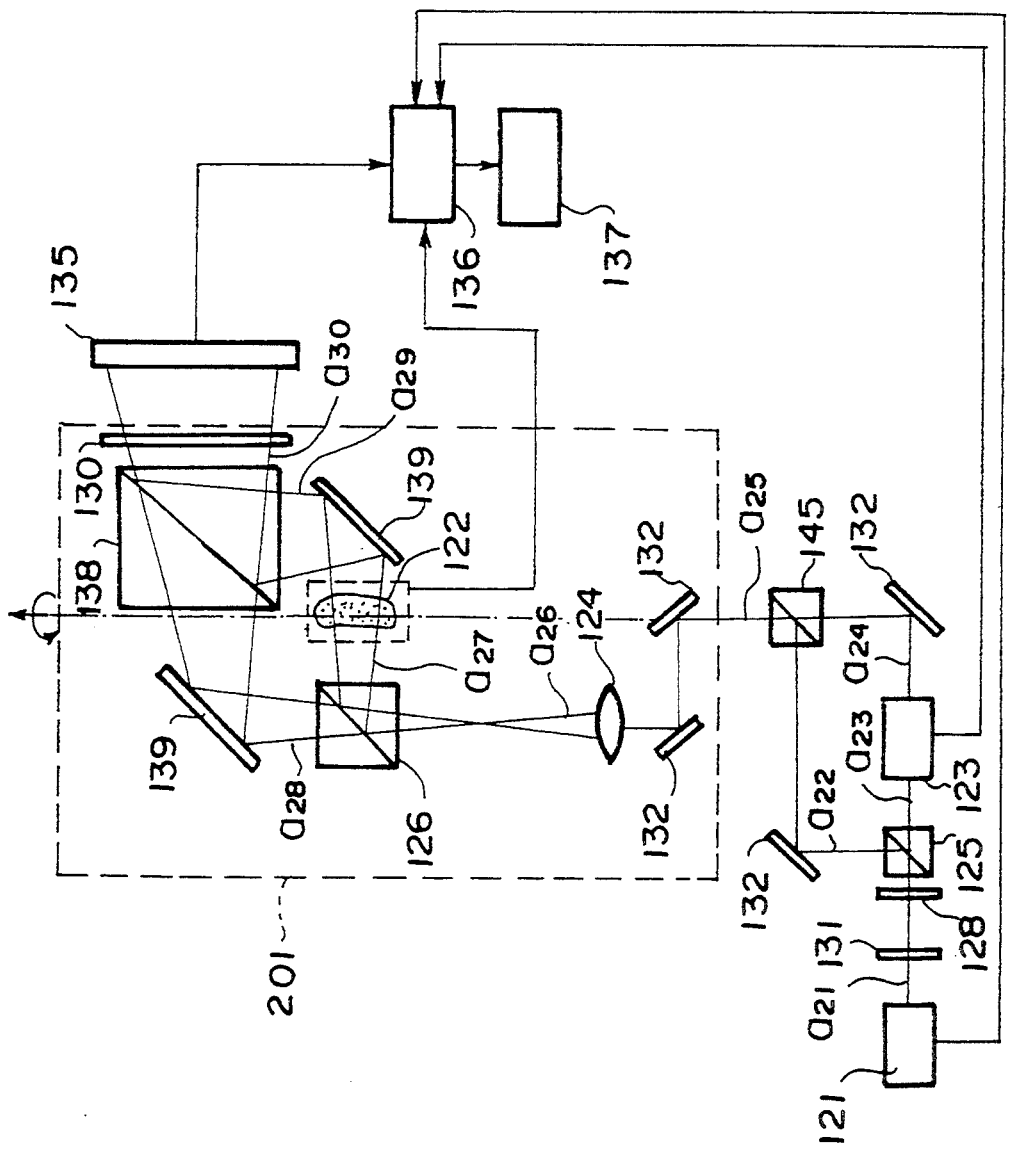

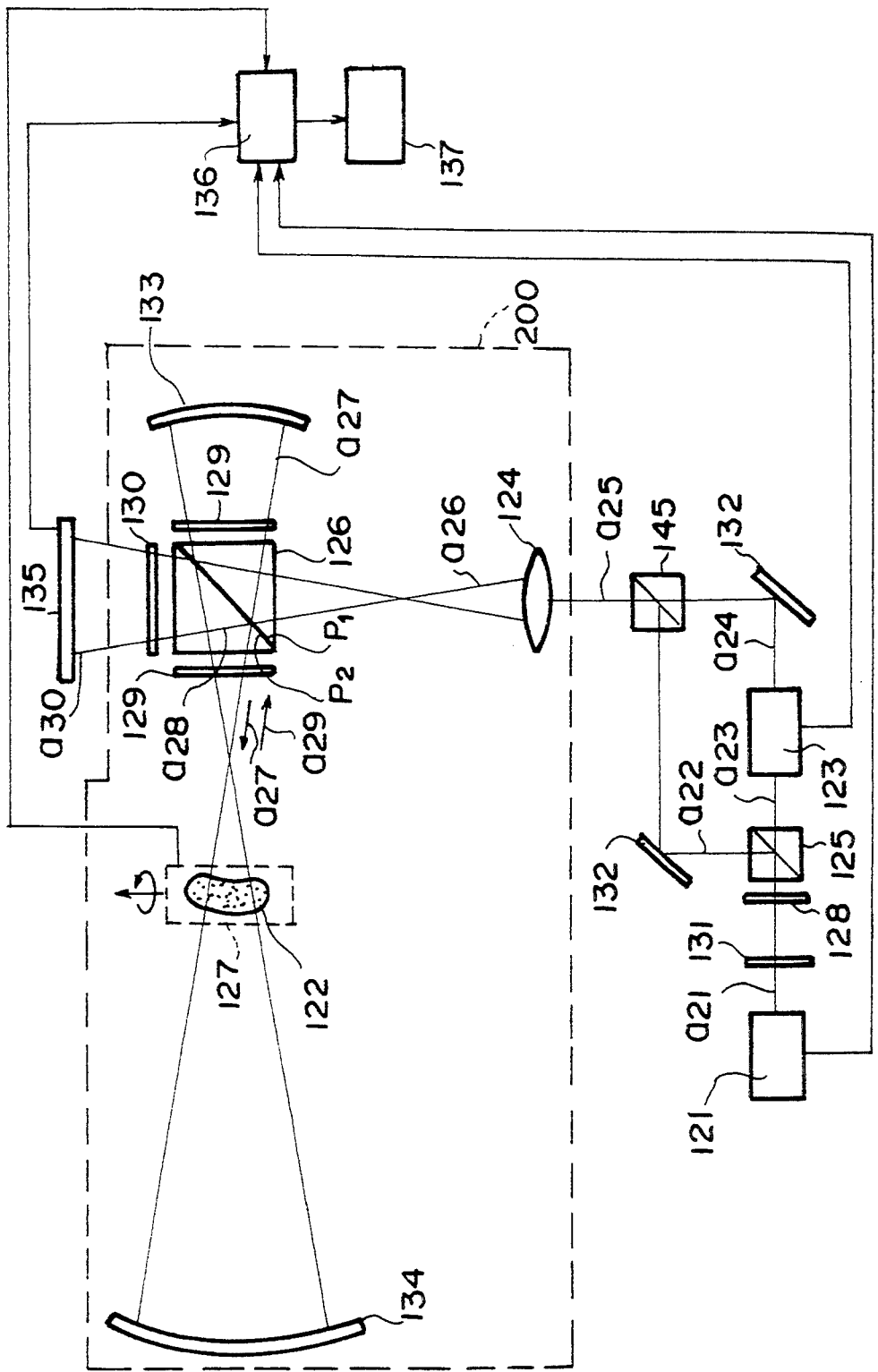

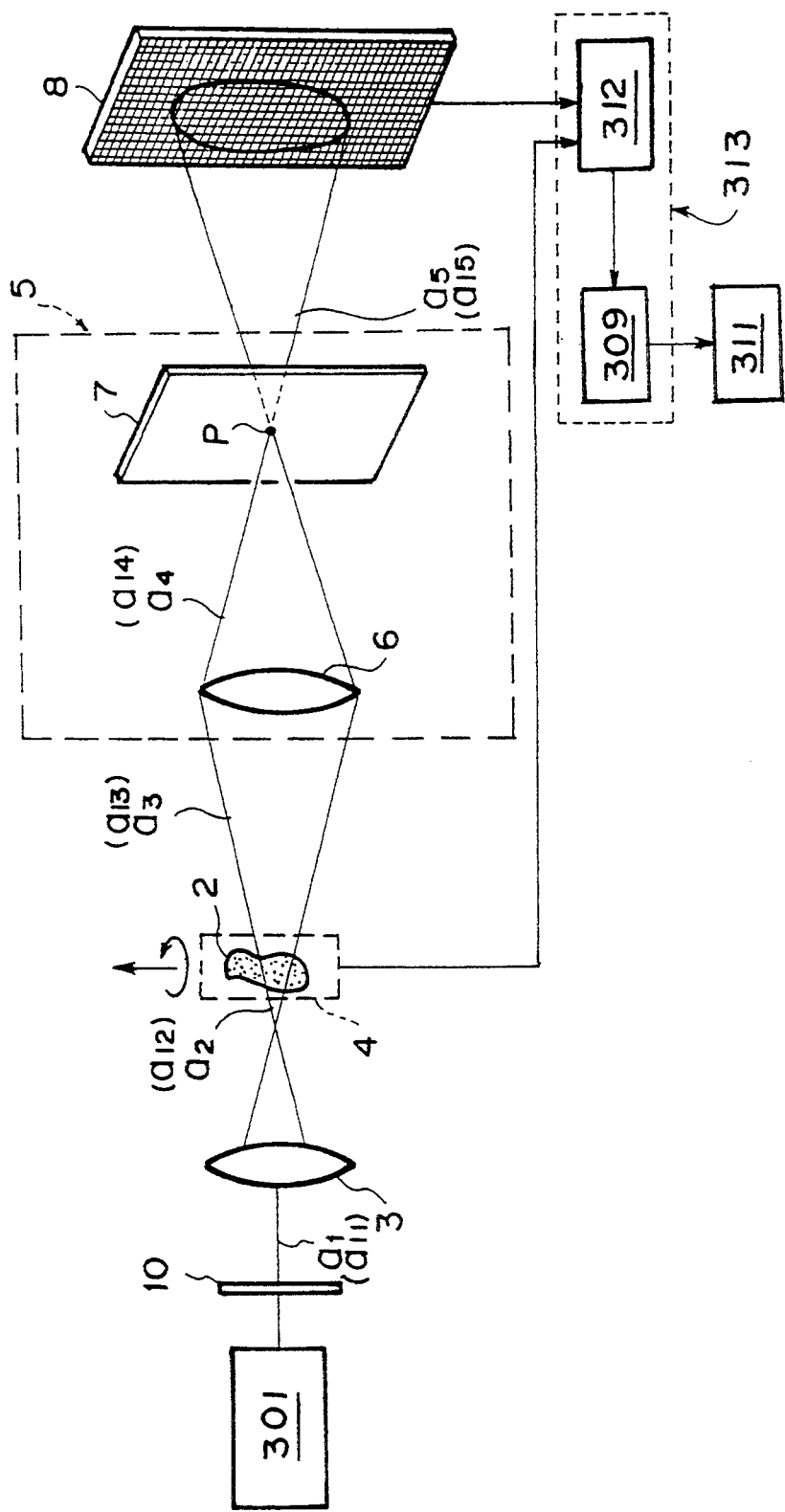

FIG. 9A

SIGNALS REPRESENTING TWO-DIMENSIONAL INTENSITY DISTRIBUTIONS OBTAINED AT RESPECTIVE SCANNED POSITIONS WITH A LASER BEAM HAVING A FREQUENCY $\nu_0$

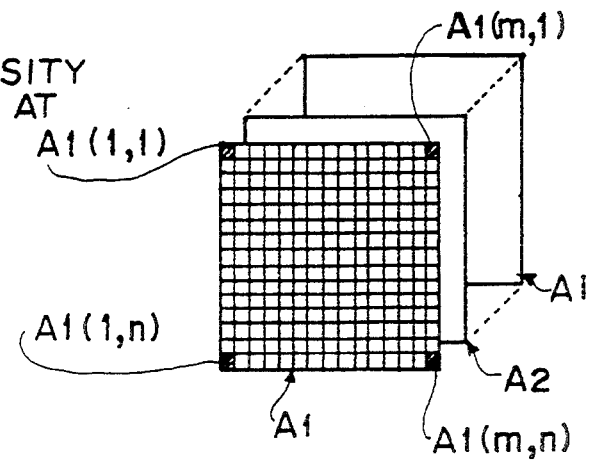

FIG. 9B

SIGNALS REPRESENTING TWO-DIMENSIONAL INTENSITY DISTRIBUTIONS OBTAINED AT RESPECTIVE SCANNED POSITIONS WITH A LASER BEAM HAVING A FREQUENCY $\nu_1$

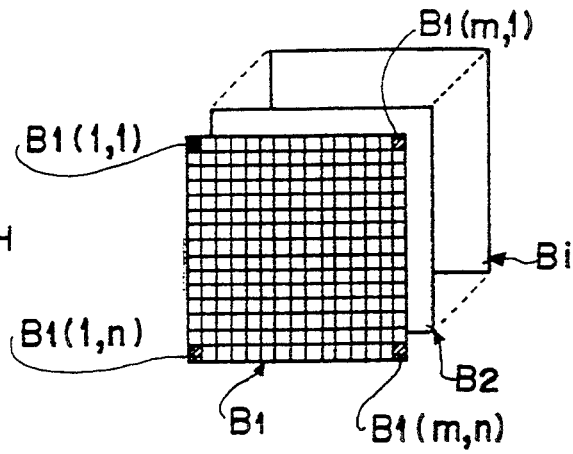

FIG. 9C

SIGNALS REPRESENTING DIFFERENCES BETWEEN TWO-DIMENSIONAL INTENSITY DISTRIBUTIONS $A_i(m,n)$ AND $B_i(m,n)$

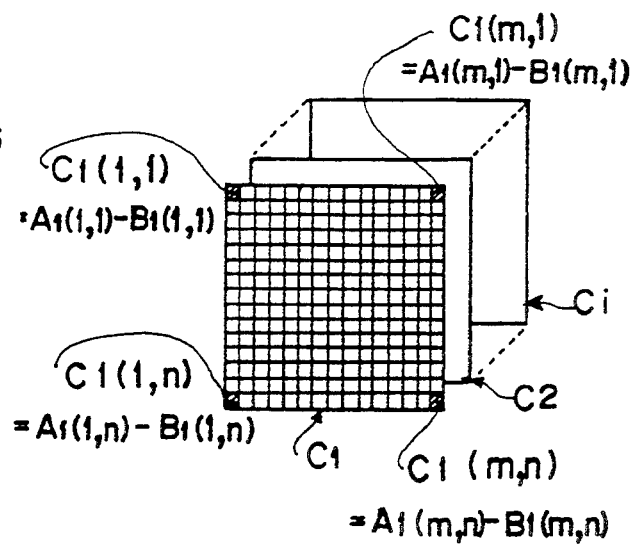

F I G. 17A
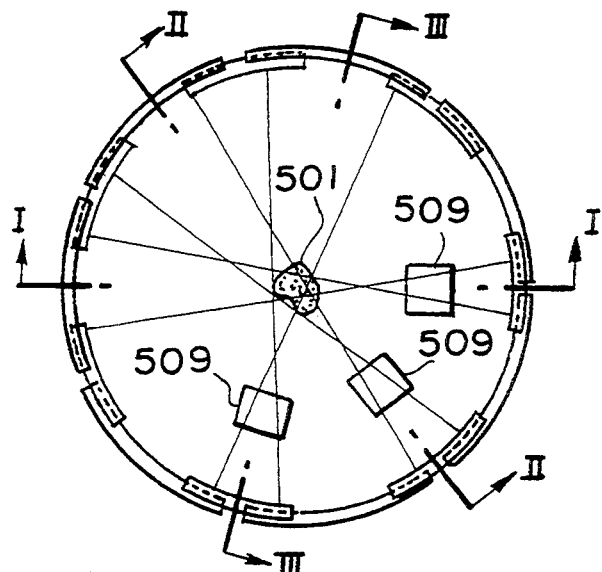
F I G. 17B
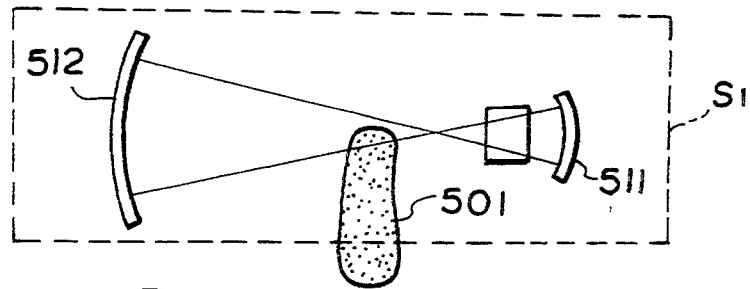
F I G. 17C
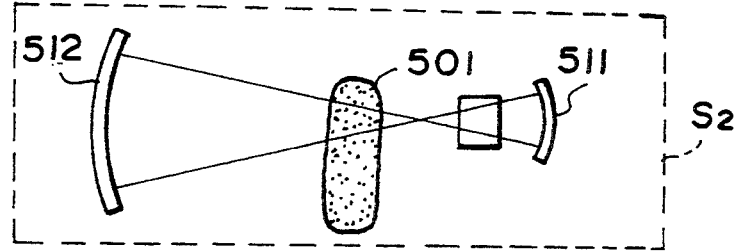
F I G. 17D
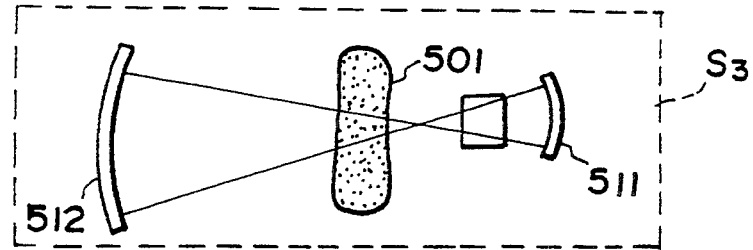

METHOD AND APPARATUS FOR OBTAINING THREE-DIMENSIONAL INFORMATION OF SAMPLES USING COMPUTER TOMOGRAPHY

BACKGROUND OF THE INVENTION

1. Field of the Invention

This invention relates to a method for obtaining three-dimensional information of a sample and an apparatus for carrying out the method. This invention particularly relates to a method and apparatus for obtaining three-dimensional information of a sample, wherein a sample is scanned with a laser beam, and three-dimensional information representing the form and/or structure of the sample, such as information representing a tomographic image or a three-dimensional image of the sample, or three-dimensional information representing constituents and/or functions of the sample is thereby obtained such that the sample may not be destroyed. This invention also relates to a method and apparatus for obtaining three-dimensional information of a sample, such as information representing a tomographic image or a three-dimensional image of the sample, wherein a sample is helically scanned with an electromagnetic wave, and three-dimensional information of the sample is thereby obtained such that the sample may not be destroyed.

2. Description of the Prior Art

It has heretofore been desired that three-dimensional information representing the form and/or structure of a sample, i.e. three-dimensional information representing the external form and/or external structure of the sample or three-dimensional information representing the internal form and/or internal structure of the sample, can be obtained such that the sample may not be destroyed. In particular, in the biological and medical fields, the sample is a living body, and therefore there is a strong demand for a technique for obtaining three-dimensional information representing the form and/or structure of the sample such that the sample may not be destroyed.

As techniques for satisfying such a demand, X-ray computed tomography (X-ray CT) and magnetic resonance imaging (MRI) enable tomographic images of samples to be obtained. However, in the strict sense, the tomographic image is two-dimensional information. Therefore, research has still been continued in order to obtain three-dimensional information of samples.

As a technique for obtaining three-dimensional information of a sample, a multilayer X-ray CT technique has been proposed. With the multilayer X-ray CT technique, a single X-ray beam is irradiated to a sample and rotated 360° along a circumference of a circle, which lies in a plane normal to an imaginary axis (hereinafter referred to as the body axis) of the sample and which has its center at the body axis. A signal representing an image of a tomographic layer of the sample is calculated from the amount of the X-ray beam, which has passed through the sample. The X-ray beam is then moved along the body axis and rotated in the same manner, and a signal representing an image of a tomographic layer of the sample is calculated in the same manner. A signal representing an image of a tomographic layer located between the two tomographic layers is interpolated from the signals representing the two tomographic layers, and three-dimensional information of the sample is thereby obtained.

The multilayer X-ray CT technique has advanced to a helical scanning X-ray CT technique, wherein an X-ray beam is moved helically around a body axis of a sample, and an image signal which is serial in the body axis direction is thereby obtained.

However, with the aforesaid X-ray CT technique and the MRI technique, three-dimensional information of a sample cannot be obtained directly. Specifically, with the aforesaid X-ray CT technique, the sample is exposed to a spot of the X-ray beam, and therefore the thus detected image is merely the line segment-like information obtained through displacement of the spot of the X-ray beam. Therefore, a helical scanning X-ray CT technique utilizing a conical beam, wherein a surface-like X-ray beam is irradiated to a sample and an image signal representing a surface-like region is thereby obtained, has been proposed in, for example, "Three-dimensional Helical Scanning CT Utilizing Conical Beam Projection" in Symposium of The Institute of Electronics and Communication Engineers of Japan, D-II, Vol. J74-D-II, No. 8, August 1991. However, no means has been developed for detecting a surface-like X-ray image, i.e. a two-dimensional X-ray image, which is obtained by the helical scanning X-ray CT technique utilizing a conical beam. Therefore, the proposed technique remains at the stage of proposal and has not yet been put into practice.

A spectroscopic analysis method is useful for identification of a substance, and therefore an attempt has been made to obtain an image, which represents an internal form and/or an internal structure of a sample, by utilizing light. Also, in the field of optics, a means for detecting light as a two-dimensional image has already been developed. For example, a charge coupled device (CCD) camera can detect light as a two-dimensional image.

Accordingly, as a method for obtaining three-dimensional information of a sample by utilizing light, a method utilizing an optical CT microscope has been known.

With the optical CT microscope, a surface-like laser beam is irradiated from an oblique direction to a sample, and the laser beam source, which produces the laser beam, is moved along a circumference of a bottom surface of a cone having its vertex at the sample. In this manner, an image of the laser beam, which has passed through the sample from different angles, is recorded by a CCD camera. An image reconstruction process utilizing the CT technique is carried out on the recorded image of the laser beam, and three-dimensional information of the sample is thereby obtained. (Such a technique is described in "Optical CT Microscope and Three-dimensional Observation," Optical Technology Contact, Vol. 28, No. 11, 1990.)

However, with the aforesaid apparatus for obtaining three-dimensional information of a sample, the direction, from which the laser beam is irradiated to the sample, is limited. Therefore, the signal representing the cross-sectional image along the directions of the passage of the laser beam cannot be obtained sufficiently, and the accuracy of the cross-sectional image cannot be kept high.

Also, during the image reconstruction process, an approximation method (Born approximation), in which the sample is limited to an approximately transparent body, is utilized. Therefore, the above-described method for obtaining three-dimensional information of a sample cannot be applied in cases where the sample contains a light scattering medium as in the cases of a living body such that scattered light is radiated out of the sample together with light, which has passed through the sample.

It has also been desired that three-dimensional information representing constituents and/or functions of a sample can be obtained such that the sample may not be destroyed. In particular, in the biological and medical fields, the sample is a living body, and therefore there is a strong demand for a technique for obtaining three-dimensional information representing constituents and/or functions of the sample such that the sample may not be destroyed.

As a method for obtaining three-dimensional information representing constituents and/or functions of a sample, a positron CT (PET) technique is known. Though the positron CT technique enables constituent information to be obtained to some extent, it has the drawbacks in that a large-sized facility, i.e. a cyclotron, must be used, and there is the risk that the sample is exposed to radiation.

A spectroscopic analysis method is useful for identification of a substance, and therefore an attempt has been made to obtain an image, which represents constituent information of a sample, by utilizing light.

For example, research has heretofore been carried out on laser beam scanning microscopes as devices utilizing a laser beam. The laser beam scanning microscopes are roughly classified into a reflection type and a transmission type. The reflection type of laser beam scanning microscope is useful for obtaining three-dimensional information representing the form and/or structure of a sample, e.g. a tomographic layer of a fluorescent sample or unevenness of a reflective sample. However, with the reflection type of laser beam scanning microscope, information representing constituents and/or functions of the sample cannot be obtained.

With the transmission type of laser beam scanning microscope, it is intended to obtain information on light absorption by constituents of a sample from the laser beam, which has passed through the sample, and thereby to obtain information representing constituents of the sample. However, the information on light absorption is obtained as a result of integration of the constituent information corresponding to the region of the sample through which the laser beam has passed. Therefore, three-dimensional information representing constituents of the sample cannot be obtained.

As a technique for solving the problems described above, the method for obtaining three-dimensional information of a sample by utilizing an optical CT microscope has been known. However, as described above, this conventional technique has various drawbacks.

SUMMARY OF THE INVENTION

The primary object of the present invention is to provide a method and apparatus for obtaining three-dimensional information representing the form and/or structure of a sample, in which a laser beam is utilized and the three-dimensional information of the sample is obtained accurately, and which is applicable also to samples containing light scattering media.

Another object of the present invention is to provide a method and apparatus for obtaining three-dimensional information representing constituents and/or functions of a sample, in which a laser beam is utilized and the three-dimensional information of the sample is obtained accurately, and which is applicable also to samples containing light scattering media.

The specific object of the present invention is to provide a method and apparatus for obtaining three-dimensional information of a sample, wherein scanning time is kept short.

The present invention provides a first method for obtaining three-dimensional information of a sample, comprising the steps of:
i) irradiating a laser beam, which has been formed into the shape of a conical beam, to a sample,
ii) displacing the laser beam with respect to the sample such that the laser beam may helically scan the sample,
iii) selecting the laser beam having passed through the sample to the same direction as the direction, along which the laser beam impinging upon the sample propagates conically, from the laser beam, which has scanned the sample and which has been radiated out of the sample, the selection being carried out by using an image forming lens and a pinhole,
iv) detecting a two-dimensional intensity distribution of the laser beam, which has passed through the sample and which has been selected, and
v) obtaining three-dimensional information representing the form and/or structure of the sample from the detected two-dimensional intensity distribution by using a computed tomography technique.

The present invention also provides an apparatus for carrying out the first method for obtaining three-dimensional information of a sample in accordance with the present invention. Specifically, the present invention also provides a first apparatus for obtaining three-dimensional information of a sample, comprising:
i) a laser beam source,
ii) an optical means for forming the laser beam, which has been produced by the laser beam source, into the shape of a conical beam,
iii) a scanning means, which irradiates the laser beam formed into the shape of the conical beam to a sample such that the laser beam may impinge as a surface beam upon the sample, and which displaces the laser beam with respect to the sample such that the laser beam may helically scan the sample,
iv) an optical direction selecting means, which condenses the laser beam having passed through the sample, and which allows a small spot formed by the condensed laser beam to pass therethrough,
v) a two-dimensional intensity detecting means, which detects a two-dimensional intensity distribution of the laser beam selected by the optical direction selecting means, and
vi) a measurement processing means, which carries out a measurement processing operation in order to obtain three-dimensional information representing the form and/or structure of the sample from the detected intensity distribution of the laser beam by using a computed tomography technique.

The term "helical" as used herein refers to the path of displacement, which is obtained from the sum of vectors representing a rotation displacement around an arbitrary axis of a sample (hereinafter referred to as the body axis) and a linear displacement along the body axis direction.

Therefore, the term "a laser beam helically scans a sample" as used herein means that, for example, the laser beam source is displaced along a helical path, and at the same time the laser beam produced by the laser beam source is irradiated to the sample. Alternatively, for example, the laser beam may be kept stationary, and the sample may be rotated around its body axis and moved along the body axis direction and may thereby be displaced with respect to the laser beam such that the sample may be helically scanned with the laser beam. As another alternative, both the laser beam and the sample may be displaced with respect to each other such that the sample may be helically scanned with the laser beam.

Also, the term "laser beam source" as used herein for the first method and apparatus for obtaining three-dimensional information of a sample in accordance with the present invention means a laser beam source, which is capable of producing a laser beam having a single wavelength, and a laser beam source, which is capable of producing laser beams having a plurality of different wavelengths and which is capable of producing a laser beam having a single wavelength for a predetermined period of time.

With the first method for obtaining three-dimensional information of a sample in accordance with the present invention, the laser beam, which has been formed into the shape of a conical beam, is irradiated to a sample. Part of the laser beam passes through the sample, and part thereof is scattered or absorbed by the outer surface and the internal substance of the sample. The laser beam is then radiated out of the sample. Of the laser beam radiated out of the sample, the laser beam, which has passed through the sample without being scattered, is condensed to a small spot by a lens of the optical direction selecting means. Only the laser beam, which has passed through the sample and which has thus been condensed, is passed through the pinhole to the two-dimensional intensity detecting means. In this manner, the laser beam, which has been scattered by the sample, is removed.

Specifically, the direction, along which the scattered laser beam is radiated out of the sample, is different from the direction, along which the laser beam impinging upon the sample propagates conically. Therefore, an image of the scattered laser beam is not formed at the small spot by the lens of the optical direction selecting means. Accordingly, the scattered laser beam does not pass through the pinhole and cannot travel to the two-dimensional intensity detecting means.

On the other hand, the direction, along which the laser beam having passed through the sample without being scattered is radiated out of the sample, coincides with the direction, along which the laser beam impinging upon the sample propagates conically. Therefore, the image of the laser beam having passed through the sample without being scattered is formed at the small spot by the lens of the optical direction selecting means. Accordingly, the laser beam having passed through the sample without being scattered passes through the pinhole and can thus travel to the two-dimensional intensity detecting means.

The laser beam, which has passed through the sample and has traveled to the two-dimensional intensity detecting means in the manner described above, projects a two-dimensional intensity distribution image, which represents an image of the sample projected by the laser beam having passed through the sample without being scattered, on the two-dimensional intensity detecting means. The two-dimensional intensity distribution image is photoelectrically converted into a signal by the two-dimensional intensity detecting means, and the obtained signal is fed into the measurement processing means.

Also, the laser beam, which has been diffused to the shape of the conical beam, is caused to helically scan the sample, and a plurality of two-dimensional intensity distribution images of the laser beam having passed through the sample without being scattered, which images correspond to the respective positions which are being scanned, are detected continuously. From the plurality of the detected two-dimensional intensity distribution images of the laser beam having passed through the sample without being scattered, three-dimensional information representing a tomographic image of the sample, a three-dimensional image of the sample, or the like, can be obtained with the measurement processing means by using the CT technique, i.e. reconstruction algorithms for conical beam projecting helical scanning.

As described above, with the first method and apparatus for obtaining three-dimensional information of a sample in accordance with the present invention, the laser beam, which has been formed into the shape of a conical beam, is helically irradiated to the sample. Therefore, the images of the sample projected by the laser beam, which has passed through the sample without being scattered, can be detected continuously from the entire circumferential positions on the sample. Accordingly, from the images of the sample projected by the laser beam, which has passed through the sample without being scattered, three-dimensional information representing the form and/or structure of the sample can be obtained accurately with respect to cross-sections taken along every direction in the sample.

Also, the optical direction selecting means makes it possible to detect only the laser beam, which has passed through the sample containing light scattering media without being scattered. Therefore, even if the sample contains light scattering media as in the cases of living bodies, the three-dimensional information of the sample can be obtained accurately.

The present invention further provides a second method for obtaining three-dimensional information of a sample, comprising the steps of:

i) irradiating a laser beam, which has been formed into the shape of a conical beam, to a sample, ii) displacing the laser beam with respect to the sample such that the laser beam may helically scan the sample, iii) matching a wave front of the laser beam, which has scanned the sample and has passed through the sample, with a wave front of a laser beam having a frequency slightly different from the frequency of the laser beam, which has scanned the sample and has passed through the sample, a wavefront-matched laser beam being thereby obtained, iv) two-dimensionally detecting the wavefront-matched laser beam with an optical heterodyne detection technique, a beat signal being thereby detected, v) measuring the intensity of the laser beam, which has passed through the sample, from the beat signal, and vi) obtaining three-dimensional information representing the form and/or structure of the sample from the intensity of the laser beam, which has passed through the sample, by using a computed tomography technique.

The present invention still further provides a third method for obtaining three-dimensional information of a sample, comprising the steps of:

i) matching a wave front of a first laser beam with a wave front of a second laser beam having a frequency slightly different from the frequency of the first laser beam, a wavefront-matched laser beam being thereby obtained, ii) forming the wavefront-matched laser beam into the shape of a conical beam, iii) splitting an optical path of the laser beam, which has been formed into the shape of a conical beam, into an optical path of a laser beam, which has the same frequency as the frequency of the first laser beam, and an optical path of a laser beam, which has the same frequency as the frequency of the second laser beam, iv) irradiating either one of the two laser beams, which respectively travel along the two split optical paths, to a sample, v) displacing the laser beam, which is irradiated to the sample, with respect to the sample such that the laser beam may helically scan the sample, vi) matching a wave front of the laser beam, which has scanned the sample and has passed through the sample, with a wave front of the other laser beam obtained by splitting the optical path, a wavefront-matched laser beam being thereby obtained from the laser beam having scanned the sample and the other laser beam, vii) two-dimensionally detecting the wavefront-matched laser beam, which has thus been obtained from the laser beam having scanned the sample and the other laser beam, with an optical heterodyne detection technique, a beat signal being thereby detected, viii) measuring the intensity of the laser beam, which has passed through the sample, from the beat signal, and ix) obtaining three-dimensional information representing the form and/or structure of the sample from the intensity of the laser beam, which has passed through the sample, by using a computed tomography technique.

The present invention also provides an apparatus for carrying out the second method for obtaining three-dimensional information of a sample in accordance with the present invention. Specifically, the present invention also provides a second apparatus for obtaining three-dimensional information of a sample, comprising:

i) a laser beam source for producing a laser beam having a single frequency, ii) an optical path splitting means, which is located in an optical path of the laser beam having been produced by the laser beam source and which splits the optical path of the laser beam into two optical paths, iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other, iv) optical means for forming the laser beams, which travel along the two split optical paths, respectively into the shapes of conical beams, v) a scanning means, which irradiates either one of the two laser beams formed into the shapes of the conical beams to a sample such that the laser beam may impinge as a surface beam upon the sample, and which displaces the laser beam with respect to the sample such that the laser beam may helically scan the sample, vi) a wavefront matching means for matching a wave front of the laser beam, which has been irradiated to the sample and has passed through the sample, with a wave front of the other laser beam formed into the shape of the conical beam, a wavefront-matched laser beam being thereby obtained, vii) a two-dimensional intensity detecting means, which is located in a plane intersecting approximately perpendicularly to the direction of travel of the wavefront-matched laser beam obtained from the wavefront matching means, and which two-dimensionally detects the optical intensity repeatedly becoming high and low at a frequency equal to the difference between the frequencies of the laser beams subjected to the wavefront matching, and viii) a measurement processing means, which detects the intensity of the laser beam having passed through the sample from the laser beam intensity detected by the two-dimensional intensity detecting means, and which carries out a measurement processing operation in order to obtain three-dimensional information representing the form and/or structure of the sample by using a computed tomography technique.

The present invention further provides an apparatus for carrying out the third method for obtaining three-dimensional information of a sample in accordance with the present invention. Specifically, the present invention further provides a third apparatus for obtaining three-dimensional information of a sample, comprising:

i) a laser beam source for producing a laser beam having a single frequency, ii) a first optical path splitting means, which is located in an optical path of the laser beam having been produced by the laser beam source and which splits the optical path of the laser beam into two optical paths, iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other, iv) a first wavefront matching means for matching a wave front of the laser beam, the frequency of which has been converted, with a wave front of the laser beam, which travels along one of the two split optical paths, a wavefront-matched laser beam being thereby obtained, v) an optical means for forming the wavefront-matched laser beam, which has been obtained from the first wavefront matching means, into the shape of a conical beam, vi) a second optical path splitting means for splitting the optical path of the laser beam, which has been formed into the shape of the conical beam, into an optical path of one of the two laser beams having slightly different frequencies and an optical path of the other laser beam, vii) a scanning means, which irradiates the laser beam, that travels along either one of the two optical paths split by the second optical path splitting means, to a sample such that the laser beam may impinge as a surface beam upon the sample, and which displaces the laser beam with respect to the sample such that the laser beam may helically scan the sample, viii) a second wavefront matching means for matching a wave front of the laser beam, which has been irradiated to the sample and has passed through the sample, with a wave front of the laser beam traveling along the other of the two optical paths split by the second optical path splitting means, a wavefront-matched laser beam being thereby obtained, ix) a two-dimensional intensity detecting means, which is located in a plane intersecting approximately perpendicularly to the direction of travel of the wavefront-matched laser beam obtained from the second wavefront matching means, and which two-dimensionally detects the optical intensity repeatedly becoming high and low at a frequency equal to the difference between the frequencies of the laser beams subjected to the wavefront matching in the second wavefront matching means, and x) a measurement processing means, which detects the intensity of the laser beam having passed through the sample from the laser beam intensity detected by the two-dimensional intensity detecting means, and which carries out a measurement processing operation in order to obtain three-dimensional information of the sample by using a computed tomography technique.

The present invention still further provides an apparatus for carrying out the third method for obtaining three-dimensional information of a sample in accordance with the present invention. Specifically, the present invention still further provides a fourth apparatus for obtaining three-dimensional information of a sample, wherein the third apparatus for obtaining three-dimensional information of a sample in accordance with the present invention is modified such that the second optical path splitting means also serves as the second wavefront matching means, and a reflection means is provided which is located at a position such that the laser beam having passed through the sample may be caused to travel to the second optical path splitting means.

The term "laser beam source for producing a laser beam having a single frequency" as used herein means a laser beam source, which is capable of producing a laser beam having a single frequency, and a laser beam source, which is capable of producing laser beams having a plurality of different frequencies (wavelengths) and which is capable of producing a laser beam having a single frequency for a predetermined period of time.

Also, in this specification, it should be understood that the frequency converting means may convert the frequency of either one of the two laser beams, which have been split by the optical path splitting means so as to follow two different optical paths, into a slightly different frequency, or may convert both the frequencies of the two laser beams such that the frequency of one of the two laser beams and the frequency of the other laser beam may become slightly different from each other.

With the second method for obtaining three-dimensional information of a sample in accordance with the present invention, the laser beam, which has been formed into the shape of a conical beam, is irradiated to a sample. Part of the laser beam passes through the sample, and part thereof is scattered or absorbed by the outer surface and the internal substance of the sample. The laser beam is then radiated out of the sample. The wave front of the laser beam, which has been radiated out of the sample, and the wave front of the other laser beam, which has a frequency slightly different from the frequency of the laser beam radiated out of the sample, are matched with each other. In this manner, of the laser beam radiated out of the sample, only the laser beam, which has passed through the sample without being scattered, is caused to interfere with the other laser beam. As a result, an interference laser beam is obtained which has an intensity repeatedly becoming high and low due to interference at a frequency equal to the difference between the frequencies of the two laser beams. The laser beam, which has been scattered by the sample, is allowed to travel without undergoing interference. The intensity of the interference laser beam is two-dimensionally detected by using the optical heterodyne detection technique, and the two-dimensional intensity distribution of the laser beam, which has passed through the sample without being scattered, is thereby detected.

Also, the laser beam, which has been formed into the shape of the conical beam, is caused to helically scan the sample, and two-dimensional intensity distributions of the laser beam having passed through the sample without being scattered, which distributions correspond to the respective positions which are being scanned, are detected continuously. From the detected two-dimensional intensity distributions of the laser beam having passed through the sample without being scattered, three-dimensional information of the sample can be obtained by using the CT technique, i.e. reconstruction algorithms for conical beam projecting helical scanning.

In the second method for obtaining three-dimensional information of a sample in accordance with the present invention, either one of the two laser beams having slightly different frequencies is irradiated to the sample, and thereafter the wave fronts of the two laser beams are matched with each other. On the other hand, with the third method for obtaining three-dimensional information of a sample in accordance with the present invention, the wave fronts of the two laser beams having slightly different frequencies are matched with each other before either one of the two laser beams impinges upon the sample. The wavefront-matched laser beam, which has thus been obtained, is formed into the shape of a conical beam, and is then split into the two laser beams having different frequencies. Either one of the two split laser beams is irradiated to the sample, and thereafter the two laser beams are caused to interfere with each other.

As described above, with the second and third methods and the second, third, and fourth apparatuses for obtaining three-dimensional information of a sample in accordance with the present invention, the laser beam, which has been formed into the shape of a conical beam, is helically irradiated to the sample. Therefore, the images of the sample projected by the laser beam, which has passed through the sample without being scattered, can be detected continuously from the entire circumferential positions on the sample. Accordingly, from the images of the sample projected by the laser beam, which has passed through the sample without being scattered, three-dimensional information representing the form and/or structure of the sample can be obtained accurately with respect to cross-sections taken along every direction in the sample.

Also, with the optical heterodyne detection technique, only the laser beam, which has passed through the sample containing light scattering media without being scattered, can be detected. Therefore, even if the sample contains light scattering media as in the cases of living bodies, the three-dimensional information representing the form and/or structure of the sample can be obtained accurately.

The present invention also provides a fourth method for obtaining three-dimensional information of a sample, comprising the steps of:
i) carrying out a measurement operation on each of at least two laser beams having different frequencies, the measurement operation comprising the steps of:
  a) forming a laser beam, which has a certain frequency, into the shape of a conical beam,
  b) irradiating the laser beam, which has been formed into the shape of the conical beam, to a sample,
  c) displacing the laser beam with respect to the sample such that the laser beam may helically scan the sample,
  d) selecting the laser beam having passed through the sample to the same direction as the direction, along which the laser beam impinging upon the sample propagates conically, from the laser beam, which has scanned the sample and which has been radiated out of the sample, the selection being carried out by using an image forming lens and a pinhole, and
  e) detecting a two-dimensional intensity distribution of the laser beam, which has passed through the sample and which has been selected, and
ii) obtaining three-dimensional information representing constituents and/or functions of the sample from the two-dimensional intensity distributions of at least two laser beams having different frequencies, which distributions have been detected by the measurement operations, by using a computed tomography technique.

The present invention further provides an apparatus for carrying out the fourth method for obtaining three-dimensional information of a sample in accordance with the present invention. Specifically, the present invention further provides a fifth apparatus for obtaining three-dimensional information of a sample, comprising:
i) a laser beam source capable of producing at least two laser beams having different frequencies,
ii) an optical means for forming a laser beam, which has been produced by the laser beam source, into the shape of a conical beam,
iii) a scanning means, which irradiates the laser beam formed into the shape of the conical beam to a sample such that the laser beam may impinge as a surface beam upon the sample, and which displaces the laser beam with respect to the sample such that the laser beam may helically scan the sample,
iv) an optical direction selecting means, which condenses the laser beam having passed through the sample, and which allows a small spot formed by the condensed laser beam to pass therethrough,
v) a two-dimensional intensity detecting means, which detects a two-dimensional intensity distribution of the laser beam selected by the optical direction selecting means, the two-dimensional intensity distribution being projected from the small spot, and
vi) a measurement processing means, which calculates values concerning constituents and/or functions of the sample from the two-dimensional intensity distributions of at least two laser beams having different frequencies, the two-dimensional intensity distributions being obtained when at least two laser beams are respectively irradiated to the sample, and which thereby obtains three-dimensional information representing constituents and/or functions of the sample.

The term "laser beam source capable of producing at least two laser beams having different frequencies" as used herein means a single laser beam source, which is capable of approximately simultaneously or sequentially producing laser beams having a plurality of different frequencies (or wavelengths), and a plurality of single-frequency laser beam sources which produce laser beams having different frequencies (or wavelengths).

With the fourth method for obtaining three-dimensional information of a sample in accordance with the present invention, the laser beam, which has been formed into the shape of a conical beam, is irradiated to a sample. Part of the laser beam passes through the sample, and part thereof is scattered or absorbed by the outer surface and the internal substance of the sample. The laser beam is then radiated out of the sample. Of the laser beam radiated out of the sample, the laser beam, which has passed through the sample without being scattered, is condensed to a small spot by a lens of the optical direction selecting means. Only the laser beam, which has passed through the sample and which has thus been condensed, is passed through the pinhole to the two-dimensional intensity detecting means. In this manner, the laser beam, which has been scattered by the sample, is removed.

Specifically, the direction, along which the scattered laser beam is radiated out of the sample, is different from the direction, along which the laser beam impinging upon the sample propagates conically. Therefore, an image of the scattered laser beam is not formed at the small spot by the lens of the optical direction selecting means. Accordingly, the scattered laser beam does not pass through the pinhole and cannot travel to the two-dimensional intensity detecting means.

On the other hand, the direction, along which the laser beam having passed through the sample without being scattered is radiated out of the sample, coincides with the direction, along which the laser beam impinging upon the sample propagates conically. Therefore, the image of the laser beam having passed through the sample without being scattered is formed at the small spot by the lens of the optical direction selecting means. Accordingly, the laser beam having passed through the sample without being scattered passes through the pinhole and can thus travel to the two-dimensional intensity detecting means.

Also, the laser beam, which has been diffused to the shape of the conical beam, is caused to helically scan the sample, and a plurality of two-dimensional intensity distribution images of the laser beam having passed through the sample without being scattered, which images correspond to the respective positions which are being scanned, are detected continuously.

The laser beam, which has passed through the sample and has traveled to the two-dimensional intensity detecting means in the manner described above, projects a two-dimensional intensity distribution image, which represents an image of the sample projected by the laser beam having passed through the sample without being scattered, on the two-dimensional intensity detecting means. The two-dimensional intensity distribution image is photoelectrically converted into a signal by the two-dimensional intensity detecting means, and the obtained signal is fed into the measurement processing means.

The measurement operation described above is carried out on each of at least two laser beams having different frequencies. In this manner, with each of at least two laser beams having different frequencies, the plurality of the two-dimensional intensity distributions of the laser beam having passed through the sample without being scattered are detected. Thereafter, from the detected two-dimensional intensity distributions corresponding to the respective laser beams, adverse effects of attenuation of the laser beams due to scattering are removed, and values concerning the constituents and/or functions of the sample are calculated. From the values concerning the constituents and/or functions of the sample and the plurality of the aforesaid two-dimensional intensity distributions, three-dimensional information representing constituents and/or functions of the sample is obtained by using the CT technique, i.e. reconstruction algorithms for conical beam projecting helical scanning.

As described above, the values concerning the constituents and/or functions of the sample are obtained by removing adverse effects of attenuation of the laser beams due to scattering from the detected two-dimensional intensity distributions corresponding to the respective laser beams. By way of example, the values concerning the constituents and/or functions of the sample can be obtained by selecting two arbitrary two-dimensional intensity distributions from the detected two-dimensional intensity distributions corresponding to the respective laser beams, and calculating the difference or the ratio between the two selected two-dimensional intensity distributions.

As described above, with the fourth method and fifth apparatus for obtaining three-dimensional information of a sample in accordance with the present invention, the optical direction selecting means makes it possible to detect only the laser beam, which has passed through the sample containing light scattering media without being scattered. Also, specific constituents and/or specific functions of the sample can be detected by irradiating at least two laser beams having different frequencies or different wavelengths to the sample.

Also, with the fourth method and fifth apparatus for obtaining three-dimensional information of a sample in accordance with the present invention, the laser beam, which has been formed into the shape of a conical beam, is helically irradiated to the sample. Therefore, the two-dimensional intensity distribution images of the sample can be detected continuously from the entire circumferential positions on the sample. Accordingly, the three-dimensional information representing constituents and/or functions of the sample can be obtained accurately with respect to cross-sections taken along every direction in the sample.

The present invention still further provides a fifth method for obtaining three-dimensional information of a sample, comprising the steps of:
i) carrying out a measurement operation on each of at least two laser beams having different frequencies, the measurement operation comprising the steps of:
  a) forming a laser beam, which has a certain frequency, into the shape of a conical beam,
  b) irradiating the laser beam, which has been formed into the shape of the conical beam, to a sample,
  c) displacing the laser beam with respect to the sample such that the laser beam may helically scan the sample,
  d) matching a wave front of the laser beam, which has scanned the sample and has passed through the sample, with a wave front of a laser beam having a frequency slightly different from the frequency of the laser beam, which has scanned the sample and has passed through the sample, a wavefront-matched laser beam being thereby obtained,
  e) two-dimensionally detecting the wavefront-matched laser beam with an optical heterodyne detection technique, a beat signal being thereby detected, and
  f) measuring the intensity of the laser beam, which has passed through the sample, from the beat signal, and
ii) obtaining three-dimensional information representing constituents and/or functions of the sample from two-dimensional intensity distributions of at least two laser beams having different frequencies, which distributions have been detected by the measurement operations, by using a computed tomography technique.

The present invention also provides an apparatus for carrying out the fifth method for obtaining three-dimensional information of a sample in accordance with the present invention. Specifically, the present invention also provides a sixth apparatus for obtaining three-dimensional information of a sample, comprising:
i) a laser beam source capable of producing at least two laser beams having different frequencies,
ii) an optical path splitting means, which is located in an optical path of a laser beam having been produced by the laser beam source and which splits the optical path of the laser beam into two optical paths,
iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other,
iv) optical means for forming the laser beams, which travel along the two split optical paths, respectively into the shapes of conical beams,
v) a scanning means, which irradiates either one of the two laser beams formed into the shapes of the conical beams to a sample such that the laser beam may impinge as a surface beam upon the sample, and which displaces the laser beam with respect to the sample such that the laser beam may helically scan the sample, vi) a wavefront matching means for matching a wave front of the laser beam, which has been irradiated to the sample and has passed through the sample, with a wave front of the other laser beam formed into the shape of the conical beam, a wavefront-matched laser beam being thereby obtained, vii) a two-dimensional intensity detecting means, which is located in a plane intersecting approximately perpendicularly to the direction of travel of the wavefront-matched laser beam obtained from the wavefront matching means, and which two-dimensionally detects the optical intensity repeatedly becoming high and low at a frequency equal to the difference between the frequencies of the laser beams subjected to the wavefront matching, and viii) a measurement processing means, which detects the intensity of the laser beam having passed through the sample from the laser beam intensity detected by the two-dimensional intensity detecting means, and which calculates values concerning constituents and/or functions of the sample from two-dimensional intensity distributions of at least two laser beams having different frequencies, the two-dimensional intensity distributions being obtained when at least two laser beams are respectively irradiated to the sample, the measurement processing means thereby obtaining three-dimensional information representing constituents and/or functions of the sample by using a computed tomography technique.

The present invention further provides an apparatus for carrying out the fifth method for obtaining three-dimensional information of a sample in accordance with the present invention. Specifically, the present invention further provides a seventh apparatus for obtaining three-dimensional information of a sample, comprising:

i) a laser beam source capable of producing at least two laser beams having different frequencies, ii) a first optical path splitting means, which is located in an optical path of a laser beam having been produced by the laser beam source and which splits the optical path of the laser beam into two optical paths, iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other, iv) a first wavefront matching means for matching a wave front of the laser beam, the frequency of which has been converted, with a wave front of the laser beam, which travels along one of the two split optical paths, a wavefront-matched laser beam being thereby obtained, v) an optical means for forming the wavefront-matched laser beam, which has been obtained from the first wavefront matching means, into the shape of a conical beam, vi) a second optical path splitting means for splitting the optical path of the laser beam, which has been formed into the shape of the conical beam, into an optical path of one of the two laser beams having slightly different frequencies and an optical path of the other laser beam, vii) a scanning means, which irradiates the laser beam, that travels along either one of the two optical paths split by the second optical path splitting means, to a sample such that the laser beam may impinge as a surface beam upon the sample, and which displaces the laser beam with respect to the sample such that the laser beam may helically scan the sample, viii) a second wavefront matching means for matching a wave front of the laser beam, which has been irradiated to the sample and has passed through the sample, with a wave front of the laser beam traveling along the other of the two optical paths split by the second optical path splitting means, a wavefront-matched laser beam being thereby obtained, ix) a two-dimensional intensity detecting means, which is located in a plane intersecting approximately perpendicularly to the direction of travel of the wavefront-matched laser beam obtained from the second wavefront matching means, and which two-dimensionally detects the optical intensity repeatedly becoming high and low at a frequency equal to the difference between the frequencies of the laser beams subjected to the wavefront matching in the second wavefront matching means, and x) a measurement processing means, which detects the intensity of the laser beam having passed through the sample from the laser beam intensity detected by the two-dimensional intensity detecting means, and which calculates values concerning constituents and/or functions of the sample from two-dimensional intensity distributions of at least two laser beams having different frequencies, the two-dimensional intensity distributions being obtained when at least two laser beams are respectively irradiated to the sample, the measurement processing means thereby obtaining three-dimensional information representing constituents and/or functions of the sample by using a computed tomography technique.

The present invention still further provides an apparatus for carrying out the fifth method for obtaining three-dimensional information of a sample in accordance with the present invention. Specifically, the present invention still further provides an eighth apparatus for obtaining three-dimensional information of a sample, wherein the seventh apparatus for obtaining three-dimensional information of a sample in accordance with the present invention is modified such that the second optical path splitting means also serves as the second wavefront matching means, and a reflection means is provided which is located at a position such that the laser beam having passed through the sample may be caused to travel to the second optical path splitting means.

With the fifth method for obtaining three-dimensional information of a sample in accordance with the present invention, a laser beam having a certain frequency is produced by the laser beam source and is formed into the shape of a conical beam. The laser beam formed into the shape of the conical beam is irradiated to a sample. Part of the laser beam passes through the sample, and part thereof is scattered or absorbed by the outer surface and the internal substance of the sample. The laser beam is then radiated out of the sample. The wave front of the laser beam, which has passed through the sample without being scattered, and the wave front of the other laser beam, which has a frequency slightly different from the frequency of the laser beam having passed through the sample without being scattered, are matched with each other. In this manner, of the laser beam radiated out of the sample, only the laser beam, which has passed through the sample without being scattered, is caused to interfere with the other laser beam. As a result, an interference laser beam is obtained which has an intensity repeatedly becoming high and low at a frequency equal to the difference between the frequencies of the two laser beams. The laser beam, which has been scattered by the sample, is allowed to travel without undergoing interference. The intensity of the interference laser beam is two-dimensionally detected by using the optical heterodyne detection technique, and the two-dimensional intensity distribution of the laser beam, which has passed through the sample without being scattered, is thereby detected.

Also, the laser beam, which has been formed into the shape of the conical beam, is caused to helically scan the sample, and two-dimensional intensity distributions of the laser beam having passed through the sample without being scattered, which distributions correspond to the respective positions which are being scanned, are detected continuously.

The measurement operation described above is carried out on each of at least two laser beams having different frequencies. In this manner, with each of at least two laser beams having different frequencies, the plurality of the two-dimensional intensity distributions of the laser beam having passed through the sample without being scattered are detected. Thereafter, from the detected two-dimensional intensity distributions corresponding to the respective laser beams, adverse effects of attenuation of the laser beams due to scattering are removed, and values concerning the constituents and/or functions of the sample are calculated. From the values concerning the constituents and/or functions of the sample and the plurality of the aforesaid two-dimensional intensity distributions, three-dimensional information representing constituents and/or functions of the sample is obtained by using the CT technique, i.e. reconstruction algorithms for conical beam projecting helical scanning.

As described above, the values concerning the constituents and/or functions of the sample are obtained by removing adverse effects of attenuation of the laser beams due to scattering from the detected two-dimensional intensity distributions corresponding to the respective laser beams. By way of example, the values concerning the constituents and/or functions of the sample can be obtained by selecting two arbitrary two-dimensional intensity distributions from the detected two-dimensional intensity distributions corresponding to the respective laser beams, and calculating the difference or the ratio between the two selected two-dimensional intensity distributions.

As described above, with the fifth method and the sixth, seventh, and eighth apparatuses for obtaining three-dimensional information of a sample in accordance with the present invention, only the laser beam, which has passed through the sample containing light scattering media without being scattered, can be detected by using the optical heterodyne detection technique. Also, specific constituents and/or specific functions of the sample can be detected by irradiating at least two laser beams having different frequencies or different wavelengths to the sample.

Also, with the fifth method and the sixth, seventh, and eighth apparatuses for obtaining three-dimensional information of a sample in accordance with the present invention, the laser beam, which has been formed into the shape of a conical beam, is helically irradiated to the sample. Therefore, the two-dimensional intensity distribution images of the sample can be detected continuously from the entire circumferential positions on the sample. Accordingly, the three-dimensional information representing constituents and/or functions of the sample can be obtained accurately with respect to cross-sections taken along every direction in the sample.

The present invention also provides a sixth method for obtaining three-dimensional information of a sample, wherein a beam of an electromagnetic wave is irradiated to a sample, the beam of the electromagnetic wave is displaced with respect to the sample such that the beam of the electromagnetic wave may helically scan the sample, the intensity of the beam of the electromagnetic wave having passed through the sample is detected, and three-dimensional information of the sample is obtained from the detected intensity of the beam of the electromagnetic wave, the method for obtaining three-dimensional information of a sample comprising the steps of:

i) irradiating a plurality of beams of the electromagnetic wave from a plurality of electromagnetic wave irradiating means to the sample, the plurality of the electromagnetic wave irradiating means being located in equally spaced relation to one another around the sample such that they may helically surround the sample at least over 360 degrees around the sample, and ii) detecting intensities of the plurality of the beams of the electromagnetic wave, which have passed through the sample, by using a plurality of electromagnetic wave detecting means, each of which is located at a position that is capable of detecting one of the beams of the electromagnetic wave having passed through the sample.

The present invention further provides a seventh method for obtaining three-dimensional information of a sample, wherein the sixth method for obtaining three-dimensional information of a sample in accordance with the present invention is modified such that the plurality of the beams of the electromagnetic wave are irradiated to the sample by sequentially causing a beam of the electromagnetic wave, which has been produced by a single electromagnetic wave producing means, to impinge upon the plurality of the electromagnetic wave irradiating means.

The present invention still further provides an apparatus for carrying out the sixth method for obtaining three-dimensional information of a sample in accordance with the present invention. Specifically, the present invention still further provides a ninth apparatus for obtaining three-dimensional information of a sample, wherein a beam of an electromagnetic wave is irradiated to a sample, the beam of the electromagnetic wave is displaced with respect to the sample such that the beam of the electromagnetic wave may helically scan the sample, the intensity of the beam of the electromagnetic wave having passed through the sample is detected, and three-dimensional information of the sample is obtained from the detected intensity of the beam of the electromagnetic wave, the apparatus for obtaining three-dimensional information of a sample comprising:

i) at least a single electromagnetic wave producing means,
ii) a plurality of electromagnetic wave irradiating means, which are located in equally spaced relation to one another around the sample such that they may helically surround the sample at least over 360 degrees around the sample, and each of which receives a beam of the electromagnetic wave having been produced by the electromagnetic wave producing means and irradiates the beam of the electromagnetic wave to the sample, and
iii) a plurality of electromagnetic wave detecting means, each of which detects the intensity of one of the beams of the electromagnetic wave having passed through the sample.

The present invention also provides an apparatus for carrying out the seventh method for obtaining three-dimensional information of a sample in accordance with the present invention. Specifically, the present invention also provides a tenth apparatus for obtaining three-dimensional information of a sample, wherein the ninth apparatus for obtaining three-dimensional information of a sample in accordance with the present invention is modified such that only a single electromagnetic wave producing means is provided, and a direction change-over means is provided which sequentially changes over the direction of travel of the beam of the electromagnetic wave having been produced by the electromagnetic wave producing means such that the beam of the electromagnetic wave may travel toward each of the plurality of the electromagnetic wave irradiating means.

The term "electromagnetic wave" as used herein means the electromagnetic wave in a narrow sense and one of electromagnetic waves in a broad sense, such as infrared rays, visible light, ultraviolet rays, X-rays, and γ-rays.

Also, the term "a beam of an electromagnetic wave helically scans a sample" as used herein means that the beam of the electromagnetic wave is displaced along a helical path and is at the same time irradiated to the sample.

Additionally, the term "a plurality of electromagnetic wave irradiating means are located such that they may helically surround a sample" as used herein means that the plurality of the electromagnetic wave irradiating means are located at predetermined intervals on a helical path having its center axis of rotation at the body axis of the sample.

Further, the term "equally spaced relation" means that the aforesaid predetermined intervals of the plurality of the electromagnetic wave irradiating means are equal to one another.

With the sixth and seventh methods for obtaining three-dimensional information of a sample in accordance with the present invention, the plurality of the electromagnetic wave irradiating means and the plurality of the electromagnetic wave detecting means are located helically around the sample. Therefore, the sample can be helically scanned with the beams of the electromagnetic wave.

Specifically, the beams of the electromagnetic wave are sequentially (or approximately simultaneously) irradiated from the plurality of the electromagnetic wave irradiating means, which are located so as to helically surround the sample, to the sample. The intensities of the beams of the electromagnetic wave having passed through the sample are detected by the electromagnetic wave detecting means. In this manner, the sample can be helically scanned with the beams of the electromagnetic wave, and signals representing the intensities of the respective beams of the electromagnetic wave having passed through the sample can be obtained.

The signals representing the intensities of the beams of the electromagnetic wave having passed through the sample have continuity with respect to the direction of the body axis of the sample. Also, the electromagnetic wave irradiating means, the electromagnetic wave detecting means, and the sample need not be moved for the scanning operation. Accordingly, the time required for the scanning operation can be kept shorter than in conventional methods and apparatuses for obtaining three-dimensional information of a sample.

BRIEF DESCRIPTION OF THE DRAWINGS

FIG. 6 is a block diagram showing a fifth embodiment of the apparatus for obtaining three-dimensional information of a sample in accordance with the present invention, FIG. 7 is a block diagram showing a sixth embodiment of the apparatus for obtaining three-dimensional information of a sample in accordance with the present invention, FIG. 8 is a block diagram showing a seventh embodiment of the apparatus for obtaining three-dimensional information of a sample in accordance with the present invention, FIGS. 9A, 9B, and 9C are explanatory views showing the effects of the seventh embodiment of the apparatus for obtaining three-dimensional information of a sample in accordance with the present invention, FIG. 17A is a perspective view showing the thirteenth embodiment of the apparatus for obtaining three-dimensional information of a sample in accordance with the present invention, the view being taken along the direction of a body axis of a sample, FIG. 17B is a sectional view taken along line I—I of FIG. 17A, FIG. 17C is a sectional view taken along line II—II of FIG. 17A, and FIG. 17D is a sectional view taken along line III—III of FIG. 17A.

DESCRIPTION OF THE PREFERRED EMBODIMENTS

The present invention will hereinbelow be described in further detail with reference to the accompanying drawings.

First, embodiments of the apparatus for obtaining three-dimensional information representing the form and/or structure of a sample will be described hereinbelow.

Figure 1:
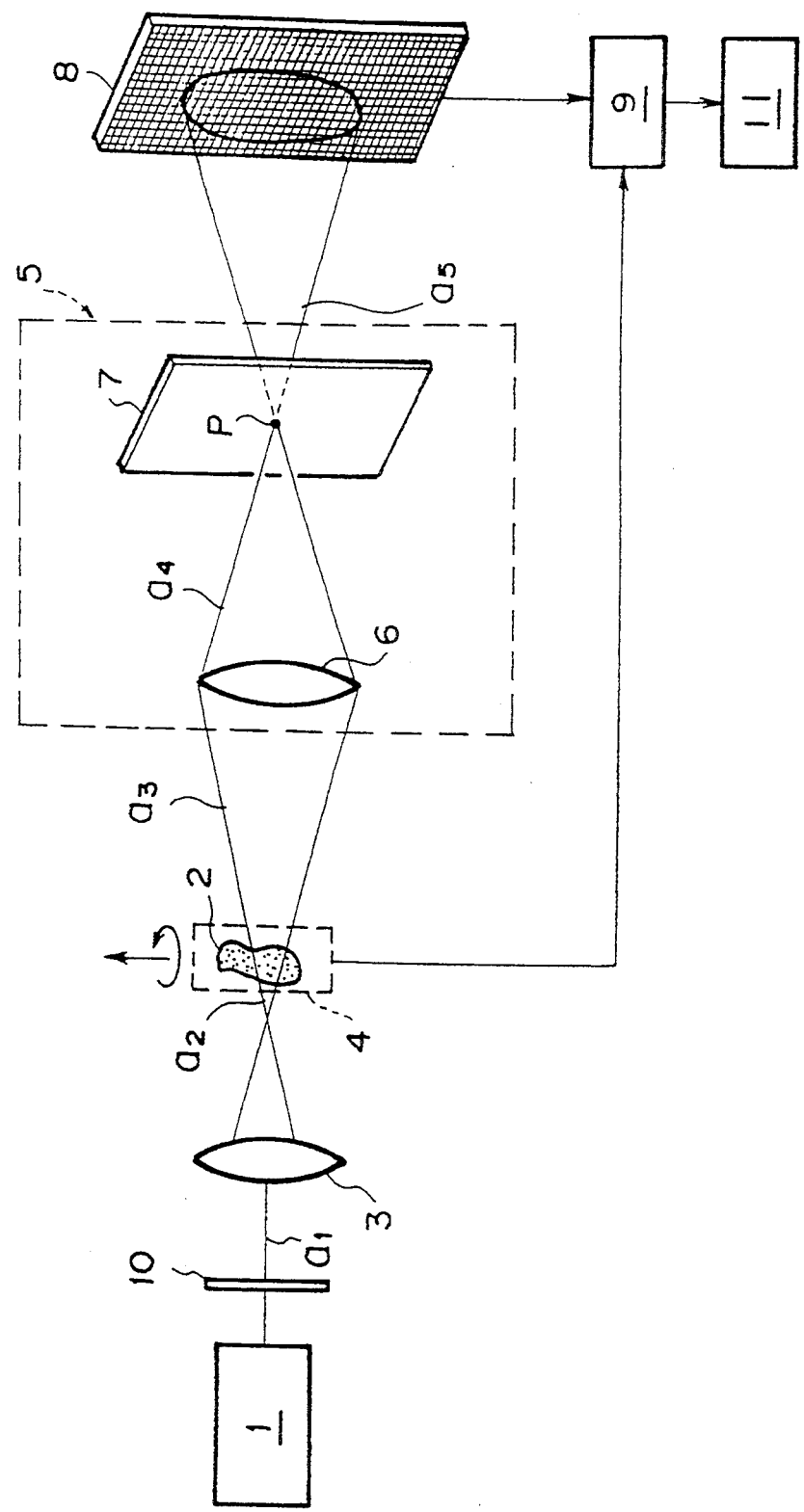
FIG. 1 is a block diagram showing a first embodiment of the apparatus for obtaining three-dimensional information of a sample in accordance with the present invention.

FIG. 1 is a block diagram showing a first embodiment of the apparatus for obtaining three-dimensional information of a sample in accordance with the present invention. This embodiment is provided with a laser beam source 1 which produces a laser beam a1. A lens 3 for forming the laser beam a1 into the shape of a conical beam a2 is located in the optical path of the laser beam a1. This embodiment is also provided with a scanning means 4, which irradiates the laser beam a2 formed into the shape of the conical beam to a sample 2 such that the laser beam a2 may impinge as a surface beam upon the sample 2, and which displaces the sample 2 such that the sample 2 may be helically scanned with the laser beam a2. Part of the laser beam a2 irradiated to the sample 2 passes through the sample 2, and part thereof is scattered or absorbed by the outer surface and the internal substance of the sample 2. A laser beam a3 is then radiated out of the sample 2. Of the laser beam a3 radiated out of the sample 2, the laser beam a3 having passed through the sample 2 to the same direction as the direction, along which the laser beam a2 impinging upon the sample 2 propagates conically, is condensed as a laser beam a4 to a small spot by a lens 6. This embodiment is further provided with a screen 7 having a pinhole P, which allows only the laser beam a4 having passed through the sample 2 and having been condensed to the small spot to pass therethrough. In FIG. 1, reference numeral 10 represents an intensity correcting plate.

The lens 6 and the screen 7 having the pinhole P together constitute an optical direction selecting means 5.

This embodiment is also provided with a two-dimensional parallel operation type of image sensor 8, which detects a two-dimensional intensity distribution image projected by a laser beam a5 having passed through the pinhole P, and which photoelectrically converts the two-dimensional intensity distribution image into a signal. A measurement processing means 9 carries out a measurement processing operation in order to obtain three-dimensional information representing the form and/or structure of the sample 2 from the signals representing the two-dimensional intensity distribution images of the laser beam a5 (i.e. the images projected by the laser beam, which has passed through the sample 2 without being scattered), which images have been detected by the image sensor 8, by using a computed tomography technique. Also, a reconstruction means 11 constructs a three-dimensional image of the sample 2, or the like, from the obtained three-dimensional information of the sample 2.

How this embodiment operates will be described hereinbelow.

The laser beam a1, which has been produced by the laser beam source 1, is formed by the lens 3 into the conical laser beam a2. The laser beam a2 impinges as a surface beam upon the sample 2. At this time, the sample 2 is displaced with respect to the laser beam a2 such that the laser beam a2 may helically scan the sample 2. Therefore, the entire circumferential surface of the sample 2 is exposed to the laser beam a2.

Part of the laser beam a2 impinging upon the sample 2 is scattered by the outer surface or the internal light scattering medium of the sample 2 and is radiated to indefinite directions out of the sample 2. Part of the laser beam a2 impinging upon the sample 2 is absorbed by the sample 2. Also, the remaining part of the laser beam a2 passes through the sample 2 and is radiated therefrom to the same direction as the direction, along which the laser beam a2 impinging upon the sample 2 propagates conically.

Therefore, the laser beam a3 thus radiated out of the sample 2 contains the laser beam a2, which has been scattered by the sample 2, and the laser beam a2, which has passed through the sample 2 without being scattered.

The laser beam a3, which has been radiated out of the sample 2, is condensed by the lens 6 of the optical direction selecting means 5 to a small spot at the pinhole P of the screen 7. At this time, the laser beam, which has been scattered to indefinite directions, impinges upon the peripheral region outward from the pinhole P. Also, the laser beam, which has passed through the sample 2 without being scattered, is condensed at the pinhole P. Therefore, only the laser beam, which has passed through the sample 2 without being scattered, passes through the pinhole P to the two-dimensional parallel operation type of image sensor 8 and projects a two-dimensional intensity distribution image of the sample 2 on the image sensor 8.

The two-dimensional intensity distribution image is detected by the image sensor 8 and photoelectrically converted into a signal. The measurement processing means 9 carries out a measurement processing operation in order to obtain three-dimensional information representing the form and/or structure of the sample 2 from the signals, which represent the two-dimensional intensity distribution images having thus been detected, and the positions on the sample 2, which are being scanned, by using the computed tomography technique. Also, the reconstruction means 11 constructs a three-dimensional image of the sample 2, a tomographic image along an arbitrary cross-section in the sample 2, or the like, from the obtained three-dimensional information of the sample 2.

As described above, with the first embodiment of the apparatus for obtaining three-dimensional information of a sample in accordance with the present invention, the sample 2 is helically scanned with the laser beam a2. Therefore, the images of the sample 2 projected by the laser beam a5, which has passed through the sample 2 without being scattered, have continuity over the entire circumference of the sample 2, and the accuracy of the tomographic images with respect to the directions, along which the laser beam has passed through the sample 2, can be kept high.

Also, the optical direction selecting means 5 makes it possible to detect only the laser beam, which has passed through the sample 2 without being scattered, from the laser beam radiated out of the sample 2. Therefore, even if the sample 2 contains a light scattering medium, the three-dimensional information representing the form and/or structure of the sample 2 can be obtained without being adversely affected by the scattered laser beam.

Figure 2:
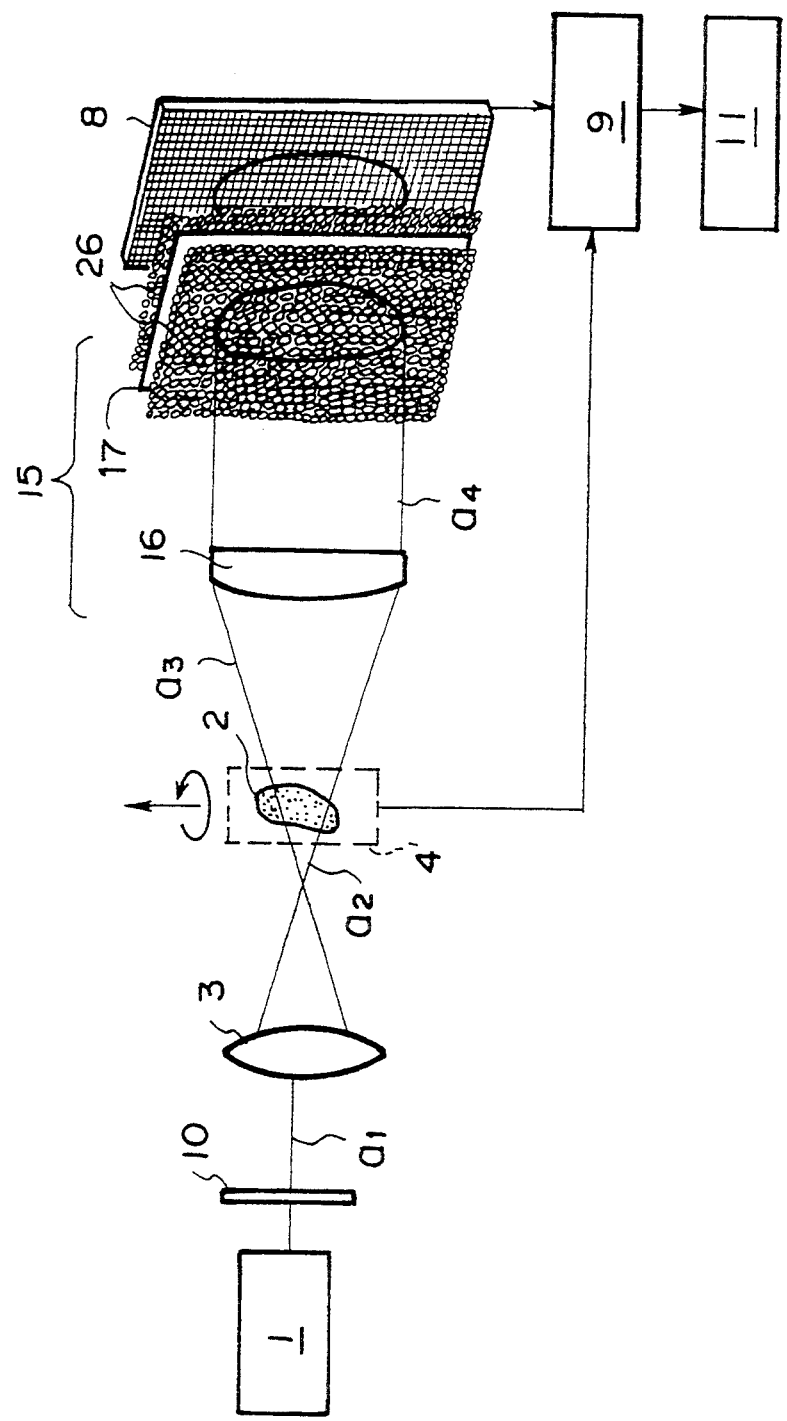
FIG. 2 is a block diagram showing a second embodiment of the apparatus for obtaining three-dimensional information of a sample in accordance with the present invention.

FIG. 2 is a block diagram showing a second embodiment of the apparatus for obtaining three-dimensional information of a sample in accordance with the present invention. The second embodiment is constituted in the same manner as that of the first embodiment, except for the structure of the optical direction selecting means.

Figure 3:
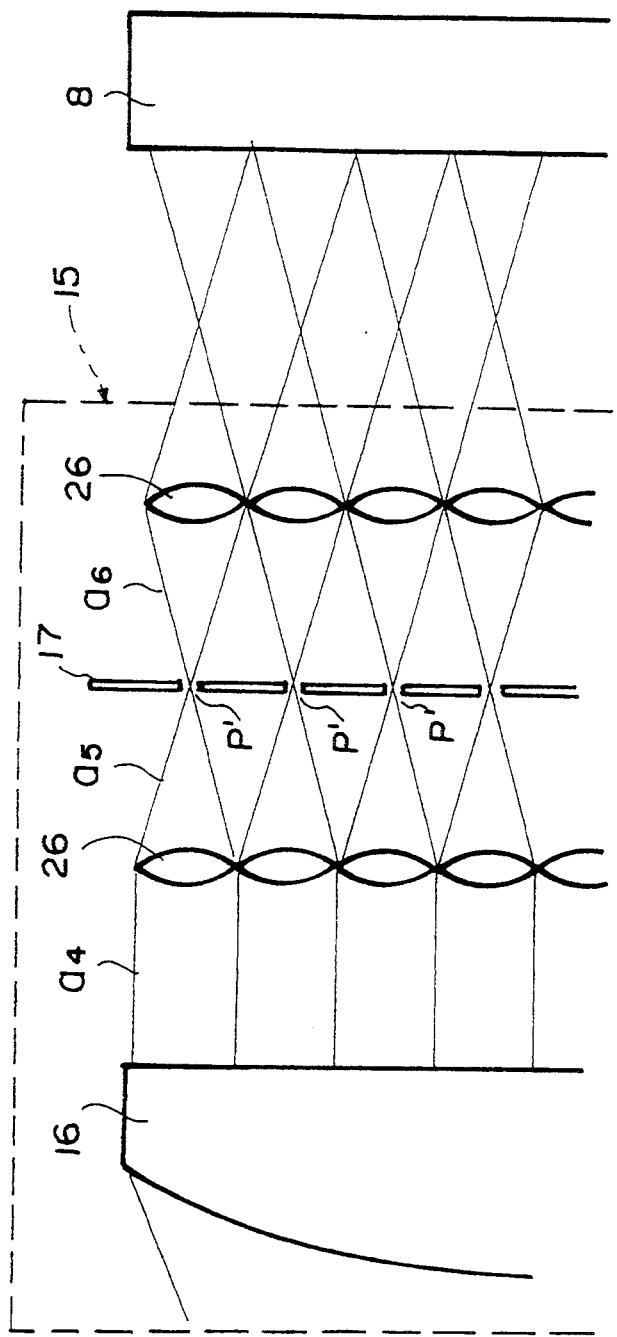
FIG. 3 is an enlarged view showing an optical direction selecting means 15 shown in FIG. 2.

Specifically, the optical direction selecting means 5 employed in the first embodiment of FIG. 1 comprises the lens 6 for selecting only the laser beam, which has passed through the sample 2 without being scattered, from the laser beam radiated out of the sample 2, and condensing the selected laser beam at the small spot, and the screen 7 having the pinhole P, which allows the laser beam having been condensed to the small spot to pass therethrough. On the other hand, the second embodiment is provided with an optical direction selecting means 15. As illustrated in FIG. 3, the optical direction selecting means 15 comprises a lens 16. Of the laser beam a3 having radiated out of the sample 2, only the laser beam, which has passed through the sample 2 without being scattered, is collimated by the lens 16 into a laser beam a4. The optical direction selecting means 15 also comprises a plurality of small lenses 26, 26, . . . , which have optical axes extending along the direction of travel of the collimated laser beam a4, and which condense a plurality of small portions of the collimated laser beam a4 to small spots of a laser beam a5. The optical direction selecting means 15 further comprises a screen 17 having pinholes P', P', . . . , which allow the plurality of the small spots of the condensed laser beam a5 to pass therethrough as a laser beam a6. The optical direction selecting means 15 still further comprises a plurality of lenses 26, 26, . . . , which prevent cross talk among the portions of the laser beam a6 having passed through the pinholes P', P', . . .

The second embodiment of FIG. 2 has the same effects as those of the first embodiment of FIG. 1.

In the first and second embodiments described above, the sample 2 need not necessarily be displaced. At least either one of the laser beam and the sample 2 may be displaced such that the laser beam may helically scan the sample 2 in the manner described above. In cases where the laser beam is displaced, it is necessary for the optical direction selecting means 5 or 15 and the image sensor 8 to be displaced in accordance with the displacement of the laser beam irradiated to the sample 2.

Figure 4:
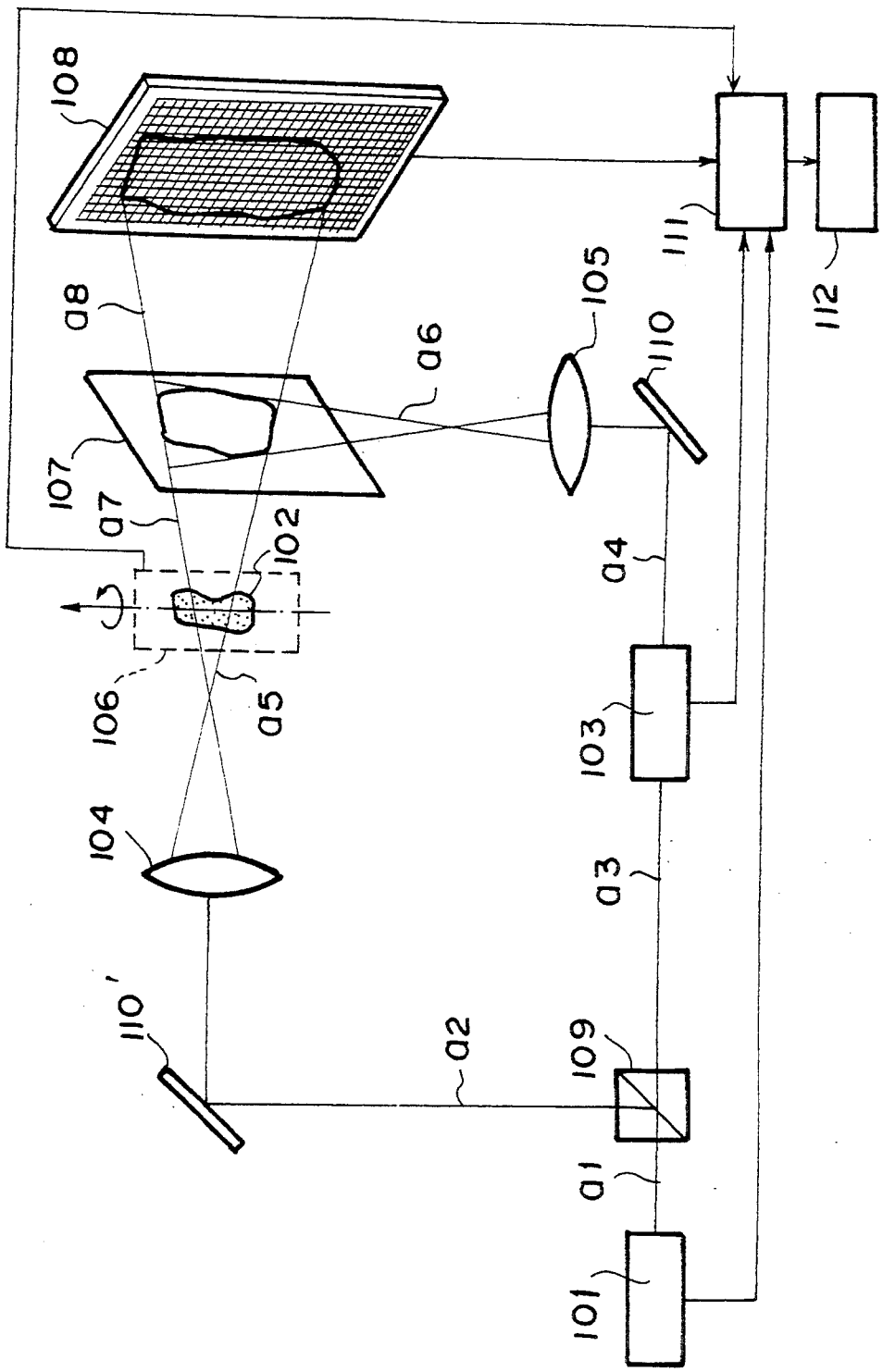
FIG. 4 is a block diagram showing a third embodiment of the apparatus for obtaining three-dimensional information of a sample in accordance with the present invention.

FIG. 4 is a block diagram showing a third embodiment of the apparatus for obtaining three-dimensional information of a sample in accordance with the present invention. This embodiment is provided with a laser beam source 101, which produces a laser beam a1 having a single frequency $\nu0$, and a semi-transparent mirror 109, which is located in the optical path of the laser beam a1 having been produced by the laser beam source 101, and which splits the optical path of the laser beam a1 into two optical paths.

Also, a frequency shifter 103 is located in one of the two optical paths split by the semi-transparent mirror 109. The frequency shifter 103 serves as a frequency converting means and converts the frequency of a laser beam a3, which travels along one of the two split optical paths, into a frequency $\nu0+\Delta\nu$ slightly different from the frequency $\nu0$ of the laser beam a1. In this manner, a laser beam a4 having the frequency $\nu0+\Delta\nu$ is obtained from the frequency shifter 103.

A lens 105 is located in the optical path of the laser beam a4 having the frequency converted by the frequency shifter 103 (in FIG. 4, in the optical path of the laser beam a4 after being reflected by a reflection mirror 110). The lens 105 forms the laser beam a4 into a conical laser beam a6.

A laser beam a2 travels along the other optical path split by the semi-transparent mirror 109. A lens 104 is located in the optical path of the laser beam a2 (in FIG. 4, in the optical path of the laser beam a2 after being reflected by a reflection mirror 110'). The lens 104 forms the laser beam a2 into a conical laser beam a5. A scanning means 106 irradiates the conical laser beam a5 such that it may impinge as a surface beam upon a sample 102. Also, the scanning means 106 displaces the sample 102 such that the laser beam a5 may helically scan the sample 102.

A beam splitter 107 serving as a wavefront matching means is located at a position that matches the wave front of the laser beam a6, which has been formed into the shape of the conical beam, with the wave front of a laser beam a7, which has been radiated out of the sample 102 after impinging upon the sample 102. A wavefront-matched laser beam a8 is thereby obtained from the beam splitter 107.

A two-dimensional parallel operation type of image sensor 108 is located in a plane, which is normal to the direction of travel of the wavefront-matched laser beam a8. The image sensor 108 detects the two-dimensional intensity distribution of the laser beam a8. A measurement processing means 111 calculates values of a signal, which represents the image of the sample 102 projected by the laser beam having passed through the sample 102 without being scattered, from the intensity of the laser beam a8 detected by the image sensor 108. The measurement processing means 111 also carries out a measurement processing operation in order to obtain three-dimensional information representing the form and/or structure of the sample 102 by using the computed tomography technique. Also, a reconstruction means 112 constructs a three-dimensional image of the sample 102, or the like, from the obtained three-dimensional information of the sample 102. The sample 102 contains a light scattering medium and is, for example, a liquid containing dispersed particles.

How the third embodiment operates will be described hereinbelow.

The laser beam a1, which has been produced by the laser beam source 101 and has the single frequency $\nu 0$, is split by the semi-transparent mirror 109 into two laser beams a2 and a3. The laser beam a3 is converted by the frequency shifter 103 into the laser beam a4 having the frequency $\nu 0 + \Delta \nu$ slightly different from the original frequency $\nu 0$.

The laser beam a2 is formed by the lens 104 into the laser beam a5 having the conical shape. The laser beam a5 is irradiated to the sample 102 such that it may impinges as a surface beam upon the sample 102.

The sample 102 is helically displaced by the scanning means 106, and the entire circumferential surface of the sample 102 is helically scanned with the laser beam a5.

Part of the laser beam a5 is scattered by the outer surface or the internal light scattering medium of the sample 102 and is radiated to indefinite directions out of the sample 102. Part of the laser beam a5 is absorbed by the outer surface or the internal substance of the sample 102. Also, the remaining part of the laser beam a5 passes through the sample 102 and is radiated therefrom to the same direction as the direction, along which the laser beam a5 impinging upon the sample 102 propagates conically. Therefore, the laser beam a7 thus radiated out of the sample 102 contains the laser beam a5, which has been scattered by the sample 102 and travels to indefinite directions, and the laser beam a5, which has passed through the sample 102 and travels to definite directions without being scattered.

In the same manner as that for the laser beam a5 having the frequency $\nu 0$, the laser beam a4 having the frequency $\nu 0 + \Delta \nu$ is formed by the lens 105 into the laser beam a6 having the conical shape. The wave front of the laser beam, which has passed through the sample 102 without being scattered and which is contained in the laser beam a7 radiated out of the sample 102, and the wave front of the laser beam a6 are matched with each other by the beam splitter 107. In this manner, the interference laser beam a8 is obtained.

The interference laser beam a8 thus obtained projects a two-dimensional intensity distribution image of the interference laser beam a8 onto the two-dimensional surface of the two-dimensional parallel operation type of image sensor 108. The two-dimensional intensity distribution image is photoelectrically converted by the image sensor 108 into a signal, and the obtained signal is fed into the measurement processing means 111, which carries out an optical heterodyne detection processing operation. In this manner, values of a signal representing the two-dimensional intensity distribution (i.e. the image of the sample 102 projected by the laser beam, which has passed through the sample 102 without being scattered) are calculated from the two-dimensional intensity distribution image of the interference laser beam a8. Also, the signals representing the two-dimensional intensity distributions of the laser beam, which correspond to the respective positions on the sample 102 that are being scanned, are subjected to the CT processing operation (i.e. the processing operation using reconstruction algorithms for conical beam projecting helical scanning), and the three-dimensional information of the sample 102 is thereby obtained. Also, the reconstruction means 112 constructs a three-dimensional image of the sample 102, a tomographic image along an arbitrary cross-section in the sample 102, or the like, from the obtained three-dimensional information of the sample 102.

With the third embodiment of the apparatus for obtaining three-dimensional information of a sample in accordance with the present invention, the sample 102 is helically scanned with the laser beam a5. Therefore, the images of the sample 102 projected by the laser beam, which has passed through the sample 102 without being scattered, have continuity over the entire circumference of the sample 102, and the accuracy of the tomographic images with respect to the directions, along which the laser beam has passed through the sample 102, can be kept high.

Also, with the third embodiment wherein the optical heterodyne detection processing operation is carried out on the laser beam radiated out of the sample 102, only the laser beam, which has passed through the sample 102 without being scattered, can be detected. Therefore, even if the sample 102 contains a light scattering medium, the three-dimensional information representing the form and/or structure of the sample 102 can be obtained without being adversely affected by the scattered laser beam.

In the third embodiment, the sample 102 is displaced. Alternatively, the sample 102 may be kept stationary, and the combination of the lens 104, the lens 105, the beam splitter 107, and the image sensor 108 may be displaced helically approximately around the sample 102. As another alternative, both the sample 102 and the combination of the lenses, and the like, may be displaced with respect to each other.

Figure 5:
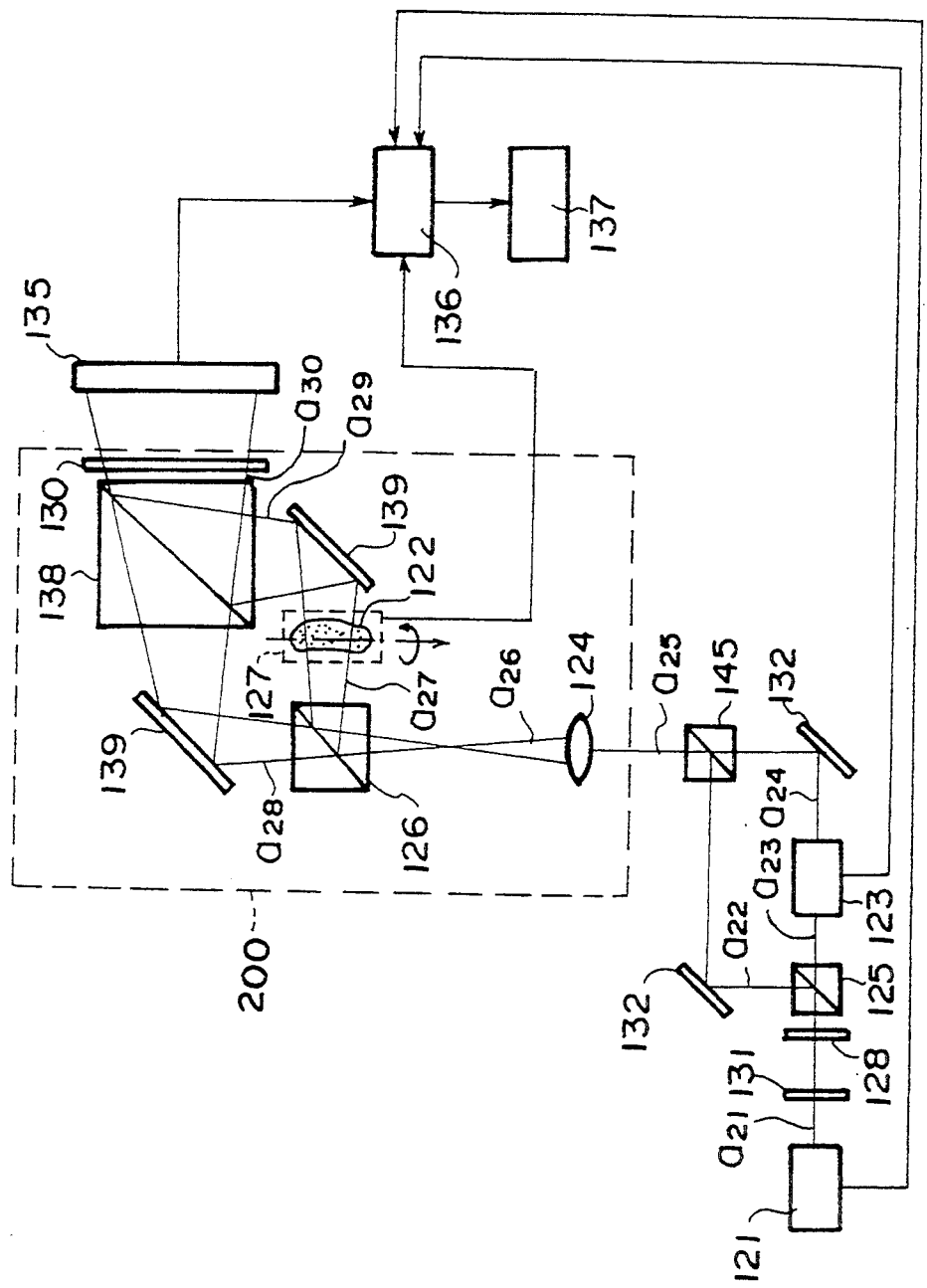
FIG. 5 is a block diagram showing a fourth embodiment of the apparatus for obtaining three-dimensional information of a sample in accordance with the present invention.

FIG. 5 is a block diagram showing a fourth embodiment of the apparatus for obtaining three-dimensional information of a sample in accordance with the present invention.

The fourth embodiment is provided with a laser beam source 121, which produces a laser beam a21 having a single frequency $\nu 0$. This embodiment is also provided with a halfwave plate 128 and a polarization beam splitter 125, which split the optical path of the laser beam a21 having been produced by the laser beam source 121 into two optical paths. Laser beams a22 and a23 travel along the two split optical paths. The planes of polarization of the laser beams a22 and a23 are normal to each other. In FIG. 5, reference numeral 131 represents an intensity correcting means, and reference numerals 132 and 139 represent mirrors.

Also, a frequency shifter 123 is located in the optical path of the laser beam a23, which follows one of the two optical paths split by the polarization beam splitter 125. The frequency shifter 123 serves as a frequency converting means and converts a frequency $\nu 0$ of the laser beam a23 into a frequency $\nu 0 + \Delta \nu$ slightly different from the frequency $\nu 0$. In this manner, a laser beam a24 having the frequency $\nu 0 + \Delta \nu$ is obtained from the frequency shifter 123.

A polarization beam splitter 145 is located at the position that matches the wave front of the laser beam a24, which has the frequency converted by the frequency shifter 123, with the wave front of the laser beam a22 which travels along the other optical path. A wavefront-matched laser beam a25 is obtained from the polarization beam splitter 145.

A lens 124 for forming the wavefront-matched laser beam a25 into a laser beam a26 having the shape of a conical beam is located in the optical path of the wavefront-matched laser beam a25. A polarization beam splitter 126 splits the optical path of the laser beam a26, which has been formed into the shape of the conical beam, into two optical paths. A laser beam a27 having a frequency $\nu0$ and a laser beam a28 having a frequency $\nu0+\Delta\nu$ travel along the two split optical paths. The planes of polarization of the laser beams a27 and a28 are normal to each other.

A scanning means 127 is located in one of the two optical paths, which have been split by the polarization beam splitter 126. The scanning means 127 irradiates the laser beam a27 such that it may impinge as a surface beam upon a sample 122. Also, the scanning means 127 displaces the sample 122 such that the laser beam a27 may helically scan the sample 122.

This embodiment is also provided with a polarization beam splitter 138 for matching the wave front of a laser beam a29, which has been radiated out of the sample 122 after impinging upon the sample 122, with the wave front of the laser beam a28, which travels along the other of the two optical paths split by the polarization beam splitter 126. This embodiment is further provided with a polarizing plate 130 for causing the components of the two laser beams subjected to the wavefront matching, which components have an identical plane of polarization, to interfere with each other. An interference laser beam a30 is thereby obtained. This embodiment is still further provided with a two-dimensional parallel operation type of image sensor 135, which detects the two-dimensional intensity distribution of the interference laser beam a30 and converts it into an electric signal. A measurement processing means 136 calculates values of a signal, which represents the image of the sample 122 projected by the laser beam having passed through the sample 122 without being scattered, from the intensity of the laser beam a30 detected by the image sensor 135. The measurement processing means 136 also carries out a measurement processing operation in order to obtain three-dimensional information representing the form and/or structure of the sample 122 from the signal representing the image of the sample 122 by using the computed tomography technique. Also, a reconstruction means 137 constructs a three-dimensional image of the sample 122, or the like, from the obtained three-dimensional information of the sample 122.

How the fourth embodiment operates will be described hereinbelow.

The laser beam a21, which has been produced by the laser beam source 121 and has the single frequency $\nu0$, is split by the halfwave plate 128 and the polarization beam splitter 125 into the laser beams a22 and a23 having the planes of polarization, which are normal to each other. The laser beam a23 is converted by the frequency shifter 123 into the laser beam a24 having the frequency $\nu0+\Delta\nu$ slightly different from the original frequency $\nu0$.

The wave fronts of two laser beams a22 and a24 having the planes of polarization, which are normal to each other, and having the slightly different frequencies, are matched with each other by the second polarization beam splitter 145. The wavefront-matched laser beam a25 is thereby obtained. The wavefront-matched laser beam a25 is formed by the lens 124 into the laser beam a26 having the shape of a conical beam.

The laser beam a26 having been formed into the shape of the conical beam is split by the polarization beam splitter 126 into the laser beam a27 having the frequency $\nu0$ and the laser beam a28 having the frequency $\nu0+\Delta\nu$.

At this time, the laser beam a27 is reflected by the polarization beam splitter 126, and the laser beam a28 passes through the polarization beam splitter 126.

The laser beam a27 reflected by the polarization beam splitter 126 is irradiated to the sample 122 such that it may impinges as a surface beam upon the sample 122. The laser beam, which has passed through the sample 122 and has been radiated out of the sample 122, is reflected as the laser beam a29 by the polarization beam splitter 138. At this time, the wave front of the laser beam, which has passed through the sample 122 without being scattered and which is contained in the laser beam a29 radiated out of the sample 122, is matched with the wave front of the laser beam a28 having the frequency $\nu0+\Delta\nu$. The components of the laser beam having passed through the sample 122 without being scattered and the laser beam a28 having the frequency $\nu0+\Delta\nu$, which components have the identical direction of polarization, are caused by the polarizing plate 130 to interfere with each other. The two-dimensional intensity distribution image of the interference laser beam a30, which has thus been obtained, is projected onto the two-dimensional parallel operation type of image sensor 135.

The sample 122 is helically displaced by the scanning means 127, and the entire circumferential surface of the sample 122 is helically scanned with the laser beam a27.

The image sensor 135, the measurement processing means 136, and the reconstruction means 137 operate in the same manner as that of the image sensor 108, the measurement processing means 111, and the reconstruction means 112, which are employed in the third embodiment described above.

in the fourth embodiment, even if a deviation occurs in the direction of incidence upon an optical system 200 for matching the wave front of the laser beam a22 having the original frequency with the wave front of the laser beam a24 having the converted frequency before the scanning of the sample 122, the wave front of the laser beam a29 having passed through the sample 122 and the wave front of the laser beam a28 having passed through the polarization beam splitter 126 can be matched with each other by the polarization beam splitter 138 such that no deviation may occur between the two laser beams a29 and a28.

The sample 122 need not necessarily be displaced by the scanning means 127. For example, as in a fifth embodiment shown in FIG. 6, the sample 122 may be kept stationary, and an optical system 201 for irradiating the laser beam to the sample 122 may be displaced helically with respect to the sample 122.

FIG. 7 is a block diagram showing a sixth embodiment of the apparatus for obtaining three-dimensional information of a sample in accordance with the present invention. In this embodiment, the polarization beam splitter 126, which is employed as the second optical path splitting means in the fourth embodiment of FIG. 5, also serves as the polarization beam splitter 138 acting as the second wavefront matching means. Also, concave mirrors 133 and 134 serving as the reflection means are located at positions that cause the laser beam having passed through the sample 122 to travel to the polarization beam splitter 126 serving as the second optical path splitting means. Further, two quarter-wave plates 129, 129 are located which rotate the plane of polarization of the laser beam and which control the reflection or the passage of the laser beam at the polarization beam splitter 126.

How the sixth embodiment operates will be described hereinbelow.

The laser beam a21, which has been produced by the laser beam source 121 and has the single frequency $\nu 0$, is split by the halfwave plate 128 and the polarization beam splitter 125 into the laser beams a22 and a23 having the planes of polarization, which are normal to each other. The laser beam a23 is converted by the frequency shifter 123 into the laser beam a24 having the frequency $\nu 0+\Delta \nu$ slightly different from the original frequency $\nu 0$.

The wave fronts of two laser beams a22 and a24 having the planes of polarization, which are normal to each other, and having the slightly different frequencies, are matched with each other by the second polarization beam splitter 145. The wavefront-matched laser beam a25 is thereby obtained. The wavefront-matched laser beam a25 is formed by the lens 124 into the laser beam a26 having the shape of a conical beam.

The laser beam a26 having been formed into the shape of the conical beam is split by the polarization beam splitter 126 into the laser beam a27 having the frequency $\nu 0$ and the laser beam a28 having the frequency $\nu 0+\Delta \nu$.

At this time, the laser beam a27 is reflected by a reflection surface P1 of the polarization beam splitter 126, and the laser beam a28 passes through the polarization beam splitter 126.

The laser beam a27 reflected by the reflection surface P1 of the polarization beam splitter 126 passes through the right quarter-wave plate 129, is reflected by the concave mirror 133 having a radius of curvature R, and again passes through the right quarter-wave plate 129. At this time, the laser beam a27 passes two times through the right quarter-wave plate 129. Therefore, the plane of polarization of the laser beam a27 is rotated 90°, and the laser beam a27 now passes through the reflection surface P1 of the polarization beam splitter 126.

The laser beam a27, which has thus passed through the polarization beam splitter 126, passes through the left quarter-wave plate 129 and is irradiated to the sample 122 such that it may impinge as a surface beam upon the sample 122. The laser beam, which has passed through the sample 122 and has been radiated out of the sample 122, is reflected by the concave mirror 134 having a radius of curvature 2R. The concave mirror 134 is located at the position facing the concave mirror 133 such that its center of curvature may coincide with the center of curvature of the concave mirror 133. The laser beam, which has been reflected by the concave mirror 134, again impinges upon the sample 122.

The laser beam, which has again impinged upon the sample 122, passes through the sample 122 and is radiated out of the sample 122 as a laser beam a29. The laser beam a29 again passes through the left quarter-wave plate 129. Therefore, the plane of polarization of the laser beam a29 is rotated 90°, and the laser beam a29 is then reflected by a reflection surface P2 of the polarization beam splitter 126. At this time, the wave front of the laser beam, which has passed through the sample 122 without being scattered and which is contained in the laser beam a29 radiated out of the sample 122, is matched with the wave front of the laser beam a28 having the frequency $\nu 0+\Delta \nu$. The components of the laser beam having passed through the sample 122 without being scattered and the laser beam a28 having the frequency $\nu 0+\Delta \nu$, which components have the identical direction of polarization, are caused by the polarizing plate 130 to interfere with each other. The two-dimensional intensity distribution image of the interference laser beam a30, which has thus been obtained, is projected onto the two-dimensional parallel operation type of image sensor 135.

The sample 122 is helically displaced by the scanning means 127, and the entire circumferential surface of the sample 122 is helically scanned with the laser beam a27.

The image sensor 135, the measurement processing means 136, and the reconstruction means 137 operate in the same manner as that of the image sensor 108, the measurement processing means 111, and the reconstruction means 112, which are employed in the third embodiment described above. In this manner, the three-dimensional information of the sample 122 is obtained, and a three-dimensional image of the sample 122, or the like, is formed. As a result, the same effects as those of the fourth embodiment shown in FIG. 5 are obtained with the sixth embodiment.

In the sixth embodiment, the sample 122 is irradiated to the laser beam two times, i.e. when the laser beam travels from the concave mirror 133 to the concave mirror 134 and when the laser beam travels from the concave mirror 134 to the polarization beam splitter 126. Therefore, the measurement processing means 136 is set such that these effects may be taken into consideration during the measurement processing operation on the image of the sample 122 projected by the laser beam, which has passed through the sample 122 without being scattered.

Embodiments of the apparatus for obtaining three-dimensional information representing constituents and/or functions of a sample will be described hereinbelow.

FIG. 8 is a block diagram showing a seventh embodiment of the apparatus for obtaining three-dimensional information of a sample in accordance with the present invention. In FIG. 8, similar elements are numbered with the same reference numerals with respect to FIG. 1. This embodiment is provided with a variable frequency laser beam source 301, which selectively and sequentially produces laser beams having arbitrary frequencies (or wavelengths). The lens 3 for forming a laser beam, which has been produced by the laser beam source 301, into the shape of a conical beam is located in the optical path of the laser beam.

This embodiment is also provided with the scanning means 4, which irradiates the laser beam formed into the shape of the conical beam to the sample 2 such that the laser beam may impinge as a surface beam upon the sample 2, and which displaces the sample 2 such that the sample 2 may be helically scanned with the laser beam. Part of the laser beam irradiated to the sample 2 passes through the sample 2, and part thereof is scattered or absorbed by the outer surface and the internal substance of the sample 2. A laser beam is then radiated out of the sample 2. Of the laser beam radiated out of the sample 2, the laser beam having passed through the sample 2 to the same direction as the direction, along which the laser beam impinging upon the sample 2 propagates conically, is condensed to a small spot by the lens 6. This embodiment is further provided with the screen 7 having the pinhole P, which allows only the laser beam having passed through the sample 2 and having been condensed to the small spot to pass therethrough.

The lens 6 and the screen 7 having the pinhole P together constitute the optical direction selecting means 5.

This embodiment is also provided with the two-dimensional parallel operation type of image sensor 8, which detects a two-dimensional intensity distribution image projected by the laser beam having passed through the pinhole P, and which photoelectrically converts the two-dimensional intensity distribution image into a signal. A calculation processing means 312 stores signals representing the two-dimensional intensity distributions, which have been detected by the image sensor 8. The calculation processing means 312 also calculates the difference between the signals representing the two-dimensional intensity distributions, which have been detected at corresponding positions on the sample 2, that are being scanned, by using two laser beams having different frequencies. A measurement means 309 obtains three-dimensional information of the sample 2 from the differences between the two-dimensional intensity distributions having been detected by using the two laser beams, which differences have been calculated by the calculation processing means 312, by using the computed tomography technique. Also, a reconstruction means 311 constructs a three-dimensional image of the sample 2, or the like, which image represents constituents and/or functions of the sample 2, from the obtained three-dimensional information of the sample 2.

The calculation processing means 312 and the measurement means 309 constitute a measurement processing means 313.

How this embodiment operates will be described hereinbelow.

A laser beam a1 having a frequency $\nu 0$ is produced by the laser beam source 1. As in the first embodiment of FIG. 1, the laser beam a1 is formed by the lens 3 into the conical laser beam a2. The laser beam a2 impinges as a surface beam upon the sample 2. At this time, the sample 2 is displaced with respect to the laser beam a2 such that the laser beam a2 may helically scan the sample 2. Therefore, the entire circumferential surface of the sample 2 is exposed to the laser beam a2.

As in the first embodiment of FIG. 1, the laser beam a3, which has been radiated out of the sample 2, contains the laser beam a2, which has been scattered by the sample 2, and the laser beam a2, which has passed through the sample 2 without being scattered. However, only the laser beam, which has passed through the sample 2 without being scattered, passes through the pinhole P to the two-dimensional parallel operation type of image sensor 8 and projects a two-dimensional intensity distribution image of the sample 2 on the image sensor 8.

The two-dimensional intensity distribution image is detected by the image sensor 8 and photoelectrically converted into a signal. A plurality of two-dimensional intensity distributions are obtained at respective positions on the sample, that are being scanned, and signals representing the two-dimensional intensity distributions are stored in the calculation processing means 312.

Thereafter, a laser beam a11 having a frequency $\nu 1$ is produced by the variable frequency laser beam source 301. In the same manner as that described above, signals representing the two-dimensional intensity distributions at respective positions on the sample, that are being scanned, are stored in the calculation processing means 312. The calculation processing means 312 then calculates the difference between the signals representing the two-dimensional intensity distributions, which have been detected at corresponding positions on the sample 2, that are being scanned, by using the two laser beams having different frequencies. The calculation processing means 312 thus detects a signal, which represents the difference between the two-dimensional intensity distributions, which have been detected at corresponding positions on the sample 2, that are being scanned.

The aforesaid effects will be described hereinbelow with reference to FIGS. 9A, 9B, and 9C. FIG. 9A shows signals representing two-dimensional intensity distributions Ai(m,n), which have been obtained at respective scanned positions A1, A2, ..., Ai by irradiating the laser beam having the frequency $\nu 0$ to the sample 2, the signals being stored in the calculation processing means 312. FIG. 9B shows signals representing two-dimensional intensity distributions Bi(m,n), which have been obtained at respective scanned positions B1, B2, ..., Bi by irradiating the laser beam having the frequency $\nu 1$ to the sample 2. The difference between the two-dimensional intensity distributions obtained at corresponding positions on the sample 2, that are being scanned, is calculated from the signals representing the two-dimensional intensity distributions Ai(m,n) and Bi(m,n), which have been obtained by irradiating the laser beam having the frequency $\nu 0$ and the laser beam having the frequency $\nu 1$ to the sample 2.

Specifically, as illustrated in FIG. 9C, values of a signal representing the difference between the two-dimensional intensity distributions are calculated with the formula $Ci(m,n) = Ai(m,n) - Bi(m,n)$. In the thus obtained signal representing the difference between the two-dimensional intensity distributions, adverse effects of attenuation of the laser beams passing through the sample 2 due to scattering can be ignored. Therefore, the signal representing the difference between the two-dimensional intensity distributions can be considered as being identical with a two-dimensional distribution signal representing the information, such as the concentration of a specific constituent of the sample 2.

The measurement means 309 carries out a CT processing operation on the signals, which represent the differences between the two-dimensional intensity distributions obtained at corresponding positions on the sample 2, that are being scanned, by using the two laser beams having different frequencies. In this manner, the three-dimensional information representing constituents of the sample 2 is obtained. The reconstruction means 311 constructs a three-dimensional image, or the like, representing the constituent information of the sample 2 from the three-dimensional information representing constituents of the sample 2.

By way of example, how the concentration of a reducing type of hemoglobin in a blood in a living body is measured three-dimensionally will be described hereinbelow.

In cases where a laser beam having a wavelength of 760 nm ($\lambda 1$) and a laser beam having a wavelength of 805 nm ($\lambda 2$) are irradiated to the sample, Formula (1) shown below obtained between an intensity $Io(\lambda)$ of the laser beam irradiated to the sample and an intensity $I(\lambda)$ of the laser beam, which has passed through the sample, according to Lambert-Beer's law.

$$\log \frac{Io(\lambda_1)}{I(\lambda_1)} - \log \frac{Io(\lambda_2)}{I(\lambda_2)} \qquad (1)$$
$$= \{\epsilon(\lambda_1) - \epsilon(\lambda_2)\}cd$$

wherein $\epsilon(\lambda)$ represents the absorption coefficient, c represents the concentration, and d represents the length of the optical path.

Formula (1) can be transformed into Formula (2).

$$d = \left\{ \log \frac{Io(\lambda_1)}{I(\lambda_1)} - \log \frac{Io(\lambda_2)}{I(\lambda_2)} \right\} / \{\epsilon(\lambda_1) - \epsilon(\lambda_2)\}c \qquad (2)$$

The right side of Formula (2) is a fixed number. Therefore, the concentration of the reducing type of hemoglobin in a blood in a living body can be detected two-dimensionally from the signal representing the two-dimensional intensity distribution.

A measurement processing operation using the CT technique is carried out on the two-dimensional distributions of the concentration of the reducing type of hemoglobin in the living body, which have thus been detected. In this manner, a three-dimensional distribution image representing the concentration of the reducing type of hemoglobin in the blood in the living body can be obtained.

Also, the concentration of an oxidizing type of hemoglobin may be detected two-dimensionally in the same manner as that described above. The ratio between the concentration of the reducing type of hemoglobin and the concentration of the oxidizing type of hemoglobin, which have been detected at each position that is being scanned, may then be calculated. In this manner, the two-dimensional distribution of the concentration of oxygen in the blood at each position that is being scanned can be detected. The measurement processing operation using the CT technique is then carried out, and a three-dimensional image representing the concentration of oxygen in the blood in the living body can thereby be obtained.

Figure 10:
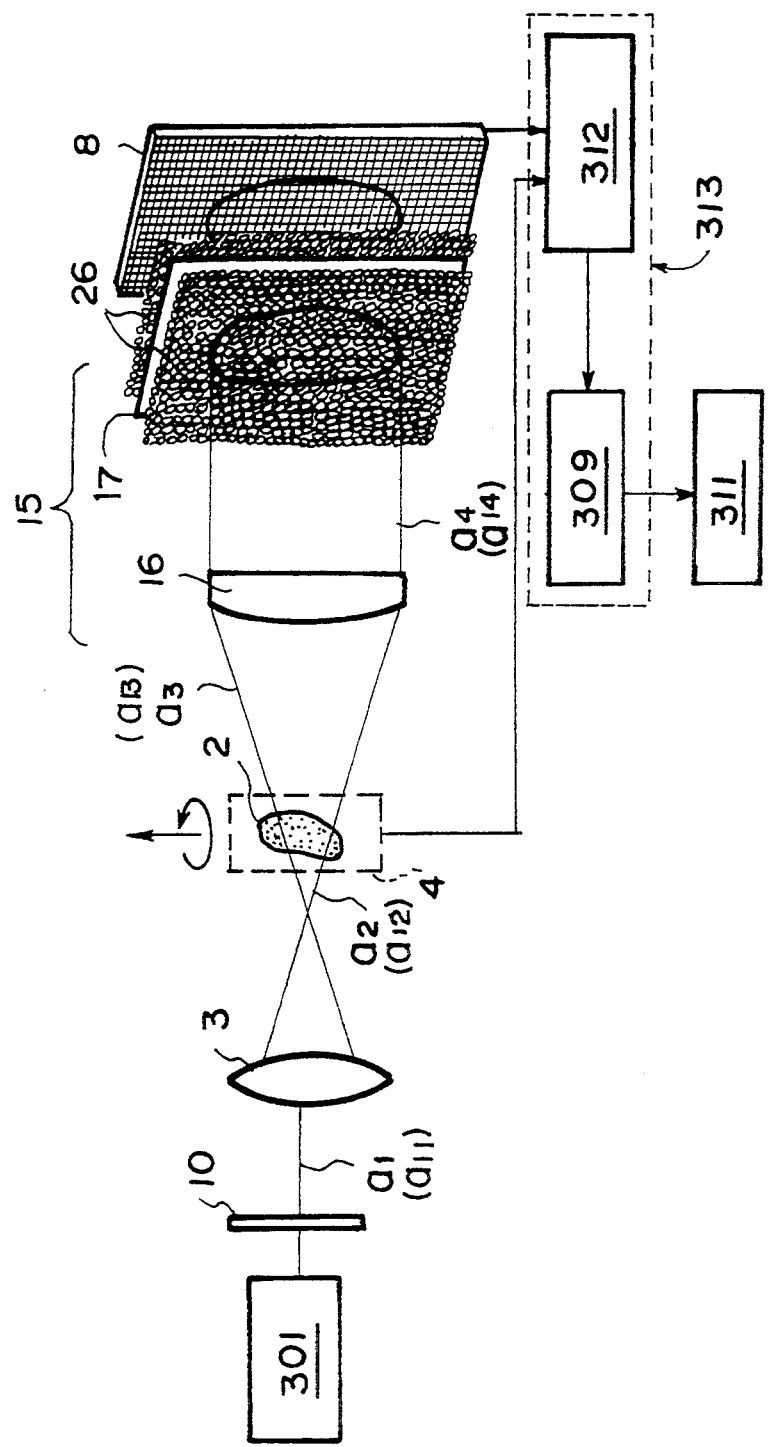
FIG. 10 is a block diagram showing an eighth embodiment of the apparatus for obtaining three-dimensional information of a sample in accordance with the present invention.

FIG. 10 is a block diagram showing an eighth embodiment of the apparatus for obtaining three-dimensional information of a sample in accordance with the present invention. The eighth embodiment is constituted in the same manner as that of the seventh embodiment, except for the structure of the optical direction selecting means. Specifically, the eighth embodiment is provided with the optical direction selecting means 15, which is employed in the second embodiment shown in FIGS. 2 and 3, in lieu of the optical direction selecting means 5 shown in FIG. 8.

The eighth embodiment of FIG. 10 has the same effects as those of the seventh embodiment of FIG. 8.

In the seventh and eighth embodiments described above, the sample 2 need not necessarily be displaced. At least either one of the laser beam and the sample 2 may be displaced such that the laser beam may helically scan the sample 2 in the manner described above. In cases where the laser beam is displaced, it is necessary for the optical direction selecting means 5 or 15 and the image sensor 8 to be displaced in accordance with the displacement of the laser beam irradiated to the sample 2.

Figure 11:
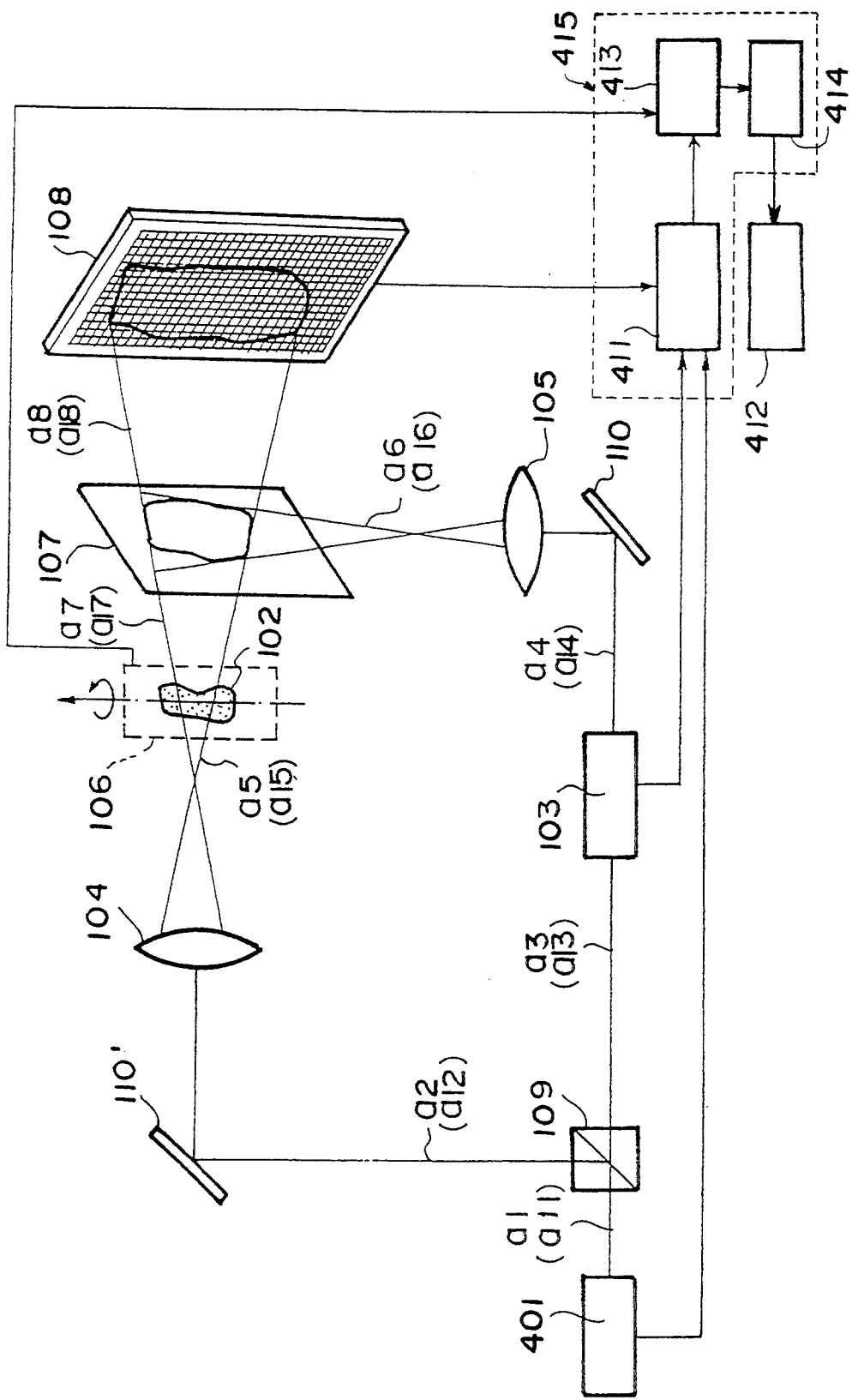
FIG. 11 is a block diagram showing a ninth embodiment of the apparatus for obtaining three-dimensional information of a sample in accordance with the present invention.

FIG. 11 is a block diagram showing a ninth embodiment of the apparatus for obtaining three-dimensional information of a sample in accordance with the present invention. In FIG. 11, similar elements are numbered with the same reference numerals with respect to FIG. 4. This embodiment is provided with a variable frequency laser beam source 401, which selectively and sequentially produces laser beams having arbitrary frequencies (or wavelengths). This embodiment is also provided with the semi-transparent mirror 109, which is located in the optical path of the laser beam having been produced by the laser beam source 401, and which splits the optical path of the laser beam into two optical paths.

Also, the frequency shifter 103 is located in one of the two optical paths split by the semi-transparent mirror 109. The frequency shifter 103 serves as a frequency converting means and converts the frequency of a laser beam, which travels along one of the two split optical paths, into a frequency slightly different from the original frequency of the laser beam.

The lens 105 is located in the optical path of the laser beam having the frequency converted by the frequency shifter 103. The lens 105 forms the laser beam having the converted frequency into a conical laser beam.

The lens 104 is located in the optical path of the laser beam, which travels along the other optical path split by the semi-transparent mirror 109. The lens 104 forms the laser beam, which travels along the other optical path, into a conical laser beam. The scanning means 106 irradiates the conical laser beam such that it may impinge as a surface beam upon the sample 102. Also, the scanning means 106 displaces the sample 102 such that the laser beam may helically scan the sample 102.

The beam splitter 107 serving as the wavefront matching means is located at the position that matches the wave front of the laser beam, which has been formed into the shape of the conical beam, with the wave front of a laser beam, which has been radiated out of the sample 102 after impinging upon the sample 102. A wavefront-matched laser beam is thereby obtained from the beam splitter 107.

The two-dimensional parallel operation type of image sensor 108 is located in a plane, which is normal to the direction of travel of the wavefront-matched laser beam. The image sensor 108 detects the two-dimensional intensity distribution of the laser beam a8. An optical heterodyne detection means 411 calculates values of a signal, which represents the image of the sample 102 projected by the laser beam having passed through the sample 102 without being scattered, from the intensity of the laser beam detected by the image sensor 108. A calculation processing means 413 stores signals representing the images of the sample 102 projected by the laser beam, which has passed through the sample without being scattered, (i.e. the signals representing the two-dimensional intensity distributions). The calculation processing means 413 also calculates the difference between the signals representing the two-dimensional intensity distributions, which have been detected at corresponding positions on the sample 102, that are being scanned, by using two laser beams having different frequencies. A measurement means 414 carries out measurements in order to obtain three-dimensional information of the sample 102 from the differences between the two-dimensional intensity distributions having been detected by using the two laser beams, which differences have been calculated by the calculation processing means 413, by using the computed tomography technique. Also, a reconstruction means 412 constructs a three-dimensional image of the sample 102, or the like, which image represents constituents and/or functions of the sample 102, from the obtained three-dimensional information of the sample 102.

The optical heterodyne detection means 411, the calculation processing means 413, and the measurement means 414 constitute a measurement processing means 415.

How the ninth embodiment operates will be described hereinbelow.

A laser beam a1 having a frequency $\nu 0$ is produced by the variable frequency laser beam source 401. As in the third embodiment of FIG. 4, the laser beam a1 is split by the semi-transparent mirror 109 into two laser beams a2 and a3. The laser beam a3 is converted by the frequency shifter 103 into the laser beam a4 having the frequency $\nu 0 + \Delta \nu$ slightly different from the original frequency $\nu 0$.

The laser beam a2 is formed by the lens 104 into the laser beam a5 having the conical shape. The laser beam a5 is irradiated to the sample 102 such that it impinges as a surface beam upon the sample 102.

The sample 102 is helically displaced by the scanning means 106, and the entire circumferential surface of the sample 102 is helically scanned with the laser beam a5.

As in the third embodiment of FIG. 4, the laser beam a7, which has been radiated out of the sample 102, contains the laser beam a5, which has been scattered by the sample 102 and travels to indefinite directions, and the laser beam a5, which has passed through the sample 102 and travels to definite directions without being scattered.

In the same manner as that for the laser beam a5 having the frequency $\nu 0$, the laser beam a4 having the frequency $\nu 0 + \Delta \nu$ is formed by the lens 105 into the laser beam a6 having the conical shape. The wave front of the laser beam, which has passed through the sample 102 without being scattered and which is contained in the laser beam a7 radiated out of the sample 102, and the wave front of the laser beam a6 are matched with each other by the beam splitter 107. In this manner, the interference laser beam a8 is obtained.

The interference laser beam a8 projects a two-dimensional intensity distribution image of the interference laser beam a8 on the two-dimensional surface of the two-dimensional parallel operation type of image sensor 108. The two-dimensional intensity distribution image is photoelectrically converted by the image sensor 108 into a signal, and the obtained signal is fed into the optical heterodyne detection means 411, which carries out an optical heterodyne detection processing operation. In this manner, values of a signal representing the two-dimensional intensity distribution (i.e. the image of the sample 102 projected by the laser beam, which has passed through the sample 102 without being scattered) are calculated from the two-dimensional intensity distribution image of the interference laser beam a8. A plurality of two-dimensional intensity distributions are obtained at respective positions on the sample, that are being scanned, and signals representing the two-dimensional intensity distributions are stored in the calculation processing means 413.

Thereafter, a laser beam a11 having a frequency $\nu 1$ is produced by the variable frequency laser beam source 401. In the same manner as that described above, signals representing the two-dimensional intensity distributions at respective positions on the sample, that are being scanned, are stored in the calculation processing means 413. The calculation processing means 413 then calculates the difference between the signals representing the two-dimensional intensity distributions, which have been detected at corresponding positions on the sample 102, that are being scanned, by using the two laser beams having different frequencies. The calculation processing means 413 thus detects a signal, which represents the difference between the two-dimensional intensity distributions, which have been detected at corresponding positions on the sample 102, that are being scanned.

The aforesaid effects will be described hereinbelow with reference to FIGS. 9A, 9B, and 9C. FIG. 9A shows signals representing two-dimensional intensity distributions Ai(m,n), which have been obtained at respective scanned positions A1, A2, . . . , Ai by irradiating the laser beam having the frequency $\nu 0$ to the sample 102, the signals being stored in the calculation processing means 413. FIG. 9B shows signals representing two-dimensional intensity distributions Bi(m,n), which have been obtained at respective scanned positions B1, B2, . . . , Bi by irradiating the laser beam having the frequency $\nu 1$ to the sample 102. The difference between the two-dimensional intensity distributions obtained at corresponding positions on the sample 102, that are being scanned, is calculated from the signals representing the two-dimensional intensity distributions Ai(m,n) and Bi(m,n), which have been obtained by irradiating the laser beam having the frequency $\nu 0$ and the laser beam having the frequency $\nu 1$ to the sample 102.

Specifically, as illustrated in FIG. 9C, values of a signal representing the difference between the two-dimensional intensity distributions are calculated with the formula $Ci(m,n) = Ai(m,n) - Bi(m,n)$. In the thus obtained signal representing the difference between the two-dimensional intensity distributions, adverse effects of attenuation of the laser beams passing through the sample 102 due to scattering can be ignored. Therefore, the signal representing the difference between the two-dimensional intensity distributions can be considered as being identical with a two-dimensional distribution signal representing the information, such as the concentration of a specific constituent of the sample 102.

The measurement means 414 carries out a CT processing operation on the signals, which represent the differences between the two-dimensional intensity distributions obtained at corresponding positions on the sample 102, that are being scanned, by using the two laser beams having different frequencies. In this manner, the three-dimensional information representing constituents of the sample 102 is obtained. The reconstruction means 412 constructs a three-dimensional image, or the like, representing the constituent information of the sample 102 from the three-dimensional information representing constituents of the sample 102.

By way of example, the concentration of the reducing type of hemoglobin in a blood in a living body can be measured three-dimensionally in the same manner as that described above with reference to Formulas (1) and (2). Also, a three-dimensional image representing the concentration of oxygen in the blood in the living body can be obtained.

In the ninth embodiment, the sample 102 is displaced. Alternatively, the sample 102 may be kept stationary, and the combination of the lens 104, the lens 105, the beam splitter 107, and the image sensor 108 may be displaced helically approximately around the sample 102. As another alternative, both the sample 102 and the combination of the lenses, and the like, may be displaced with respect to each other.

Figure 12:
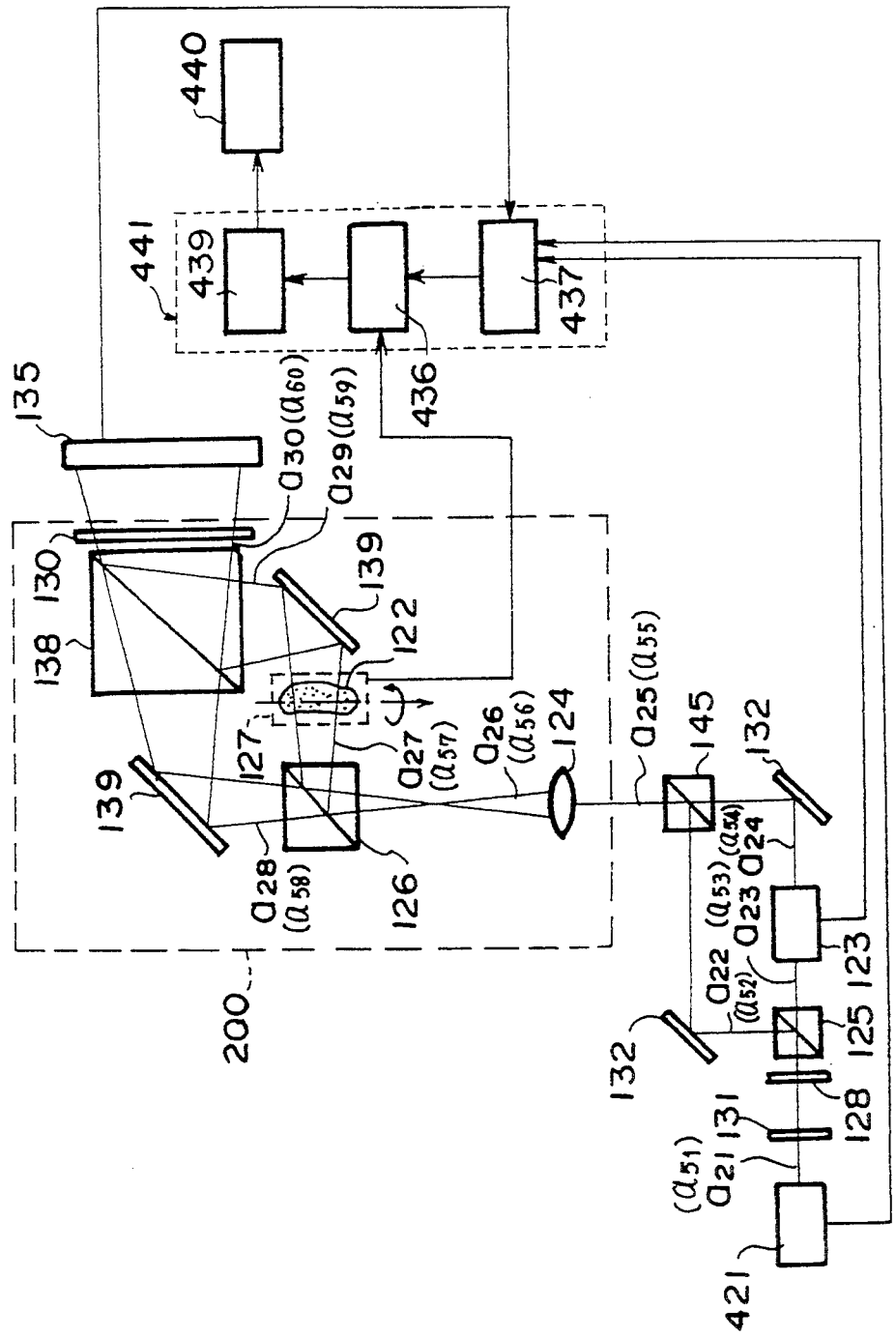
FIG. 12 is a block diagram showing a tenth embodiment of the apparatus for obtaining three-dimensional information of a sample in accordance with the present invention.

FIG. 12 is a block diagram showing a tenth embodiment of the apparatus for obtaining three-dimensional information of a sample in accordance with the present invention. In FIG. 12, similar elements are numbered with the same reference numerals with respect to FIG. 5. This embodiment is provided with a variable frequency laser beam source 421, which selectively and sequentially produces laser beams having arbitrary frequencies (or wavelengths). This embodiment is also provided with the halfwave plate 128 and the polarization beam splitter 125, which split the optical path of the laser beam having been produced by the laser beam source 421 into two optical paths. The planes of polarization of the laser beams traveling along the two split optical paths are normal to each other.

Also, the frequency shifter 123 is located in the optical path of the laser beam, which follows one of the two optical paths split by the polarization beam splitter 125. The frequency shifter 123 serves as the frequency converting means and converts a frequency $\nu 0$ of the laser beam into a frequency $\nu 0 + \Delta \nu$ slightly different from the frequency $\nu 0$. In this manner, a laser beam having the frequency $\nu 0 + \Delta \nu$ is obtained from the frequency shifter 123.

The polarization beam splitter 145 is located at the position that matches the wave front of the laser beam, which has the frequency converted by the frequency shifter 123, with the wave front of the laser beam which travels along the other optical path. A wavefront-matched laser beam is obtained from the polarization beam splitter 145.

The lens 124 for forming the wavefront-matched laser beam into a laser beam having the shape of a conical beam is located in the optical path of the wavefront-matched laser beam. The polarization beam splitter 126 splits the optical path of the laser beam, which has been formed into the shape of the conical beam, into two optical paths. A laser beam having a frequency $\nu 0$ and a laser beam having a frequency $\nu 0 + \Delta \nu$ travel along the two split optical paths. The planes of polarization of the laser beams traveling along these two split optical paths are normal to each other.

The scanning means 127 is located in one of the two optical paths, which have been split by the polarization beam splitter 126. The scanning means 127 irradiates one of the split laser beams such that it may impinge as a surface beam upon the sample 122. Also, the scanning means 127 displaces the sample 122 such that the laser beam may helically scan the sample 122.

This embodiment is also provided with the polarization beam splitter 138 for matching the wave front of a laser beam, which has been radiated out of the sample 122 after impinging upon the sample 122, with the wave front of the laser beam, which travels along the other of the two optical paths split by the polarization beam splitter 126. This embodiment is further provided with the polarizing plate 130 for causing the components of the two laser beams subjected to the wavefront matching, which components have an identical plane of polarization, to interfere with each other. An interference laser beam is thereby obtained. This embodiment is still further provided with the two-dimensional parallel operation type of image sensor 135, which detects the two-dimensional intensity distribution of the interference laser beam and converts it into an electric signal. An optical heterodyne detection means 437 calculates values of a signal, which represents the image of the sample 122 projected by the laser beam having passed through the sample 122 without being scattered, from the intensity of the laser beam detected by the image sensor 135o A calculation processing means 436 stores signals representing the images of the sample 122 projected by the laser beam, which has passed through the sample without being scattered, (i.e. the signals representing the two-dimensional intensity distributions). The calculation processing means 436 also calculates the difference between the signals representing the two-dimensional intensity distributions, which have been detected at corresponding positions on the sample 122, that are being scanned, by using two laser beams having different frequencies. A measurement means 439 obtains three-dimensional information of the sample 122 from the differences between the two-dimensional intensity distributions having been detected by using the two laser beams, which differences have been calculated by the calculation processing means 436, by using the computed tomography technique. Also, a reconstruction means 440 constructs a three-dimensional image of the sample 122, or the like, which image represents constituents and/or functions of the sample 122, from the obtained three-dimensional information of the sample 122.

The optical heterodyne detection means 437, the calculation processing means 436, and the measurement means 439 constitute a measurement processing means 441.

How the tenth embodiment operates will be described hereinbelow.

A laser beam a21 having a frequency $\nu 0$ is produced by the variable frequency laser beam source 421. The laser beam a21 is split by the halfwave plate 128 and the polarization beam splitter 125 into the laser beams a22 and a23 having the planes of polarization, which are normal to each other. The laser beam a23 is converted by the frequency shifter 123 into the laser beam a24 having the frequency $\nu 0 + \Delta \nu$ slightly different from the original frequency $\nu 0$.

The wave fronts of two laser beams a22 and a24 having the planes of polarization, which are normal to each other, and having the slightly different frequencies, are matched with each other by the second polarization beam splitter 145. The wavefront-matched laser beam a25 is thereby obtained. The wavefront-matched laser beam a25 is formed by the lens 124 into the laser beam a26 having the shape of a conical beam.

The laser beam a26 having been formed into the shape of the conical beam is split by the polarization beam splitter 126 into the laser beam a27 having the frequency $\nu 0$ and the laser beam a28 having the frequency $\nu 0 + \Delta \nu$.

At this time, the laser beam a27 is reflected by the polarization beam splitter 126, and the laser beam a28 passes through the polarization beam splitter 126.

The laser beam a27 reflected by the polarization beam splitter 126 is irradiated to the sample 122 such that it may impinges as a surface beam upon the sample 122. The laser beam, which has passed through the sample 122 and has been radiated out of the sample 122, is reflected as the laser beam a29 by the polarization beam splitter 138. At this time, the wave front of the laser beam, which has passed through the sample 122 without being scattered and which is contained in the laser beam a29 radiated out of the sample 122, is matched with the wave front of the laser beam a28 having the frequency ν0+Δν. The components of the laser beam having passed through the sample 122 without being scattered and the laser beam a28 having the frequency ν0+Δν, which components have the identical direction of polarization, are caused by the polarizing plate 130 to interfere with each other. The two-dimensional intensity distribution image of the interference laser beam a30, which has thus been obtained, is projected onto the two-dimensional parallel operation type of image sensor 135. The two-dimensional intensity distribution image is photoelectrically converted by the image sensor 135 into a signal, and the obtained signal is fed into the optical heterodyne detection means 437, which carries out an optical heterodyne detection processing operation. In this manner, values of a signal representing the two-dimensional intensity distribution (i.e. the image of the sample 122 projected by the laser beam, which has passed through the sample 122 without being scattered) are calculated from the two-dimensional intensity distribution image of the interference laser beam a30. A plurality of two-dimensional intensity distributions are obtained at respective positions on the sample, that are being scanned, and signals representing the two-dimensional intensity distributions are stored in the calculation processing means 436.

The sample 122 is helically displaced by the scanning means 127, and the entire circumferential surface of the sample 122 is helically scanned with the laser beam a27.

Thereafter, a laser beam a51 having a frequency ν1 is produced by the variable frequency laser beam source 421. In the same manner as that described above, signals representing the two-dimensional intensity distributions at respective positions on the sample, that are being scanned, are stored in the calculation processing means 436. The calculation processing means 436 then calculates the difference between the signals representing the two-dimensional intensity distributions, which have been detected at corresponding positions on the sample 122, that are being scanned, by using the two laser beams having different frequencies. The calculation processing means 436 thus detects a signal, which represents the difference between the two-dimensional intensity distributions, which have been detected at corresponding positions on the sample 122, that are being scanned.

The measurement means 439 carries out a CT processing operation on the signals, which represent the differences between the two-dimensional intensity distributions obtained at corresponding positions on the sample 122, that are being scanned, by using the two laser beams having different frequencies. In this manner, the three-dimensional information representing constituents of the sample 122 is obtained. The reconstruction means 440 constructs a three-dimensional image, or the like, representing the constituent information of the sample 122 from the three-dimensional information representing constituents of the sample 122.

In the tenth embodiment, even if a deviation occurs in the direction of incidence upon the optical system 200 for matching the wave front of the laser beam a22 having the original frequency with the wave front of the laser beam a24 having the converted frequency before the scanning of the sample 122, the wave front of the laser beam a29 having passed through the sample 122 and the wave front of the laser beam a28 having passed through the polarization beam splitter 126 can be matched with each other by the polarization beam splitter 138 such that no deviation may occur between the two laser beams a29 and a28.

Figure 13:
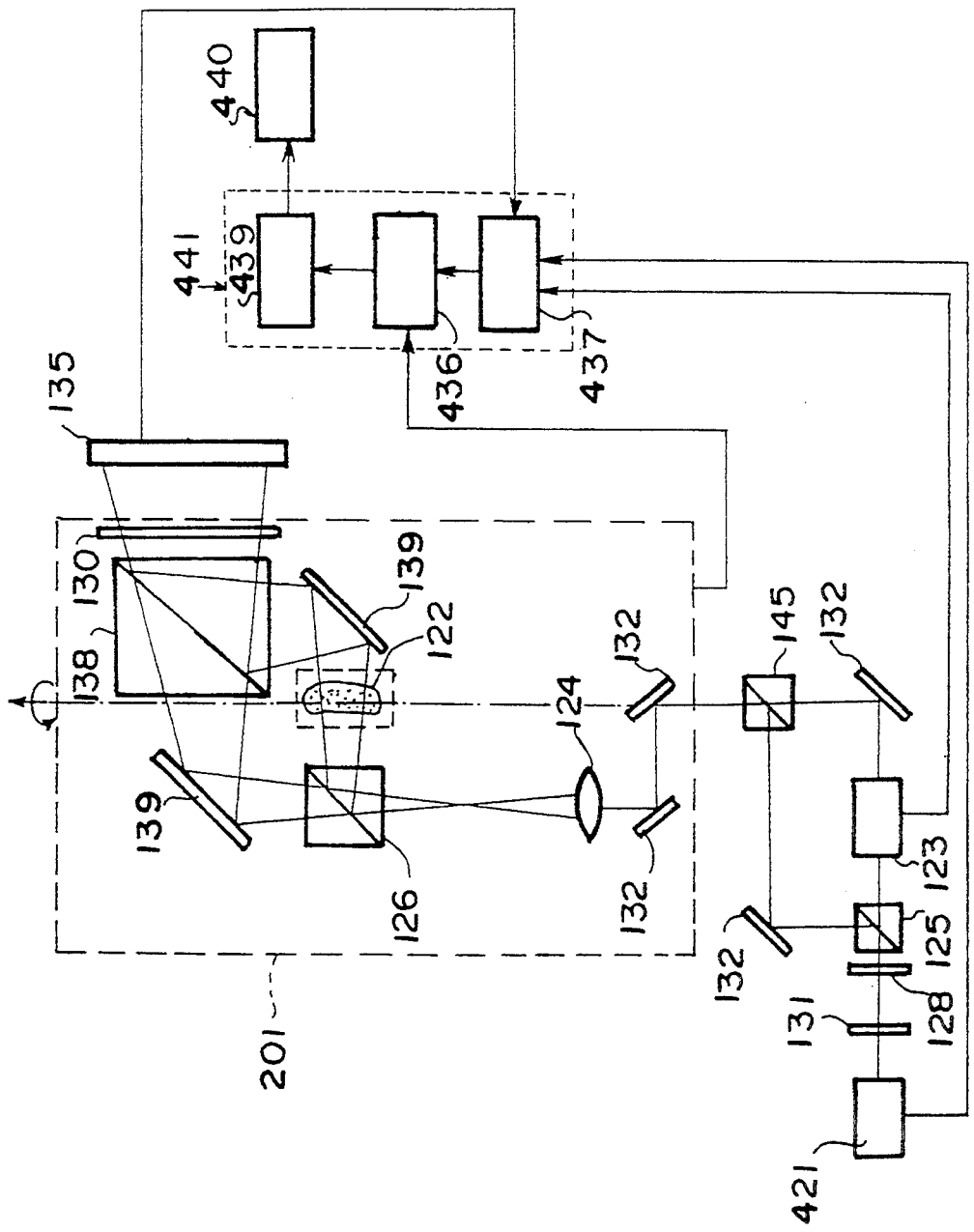
FIG. 13 is a block diagram showing an eleventh embodiment of the apparatus for obtaining three-dimensional information of a sample in accordance with the present invention.

The sample 122 need not necessarily be displaced by the scanning means 127. For example, as in an eleventh embodiment shown in FIG. 13, the sample 122 may be kept stationary, and the optical system 201 for irradiating the laser beam to the sample 122 may be displaced helically with respect to the sample 122.

Figure 14:
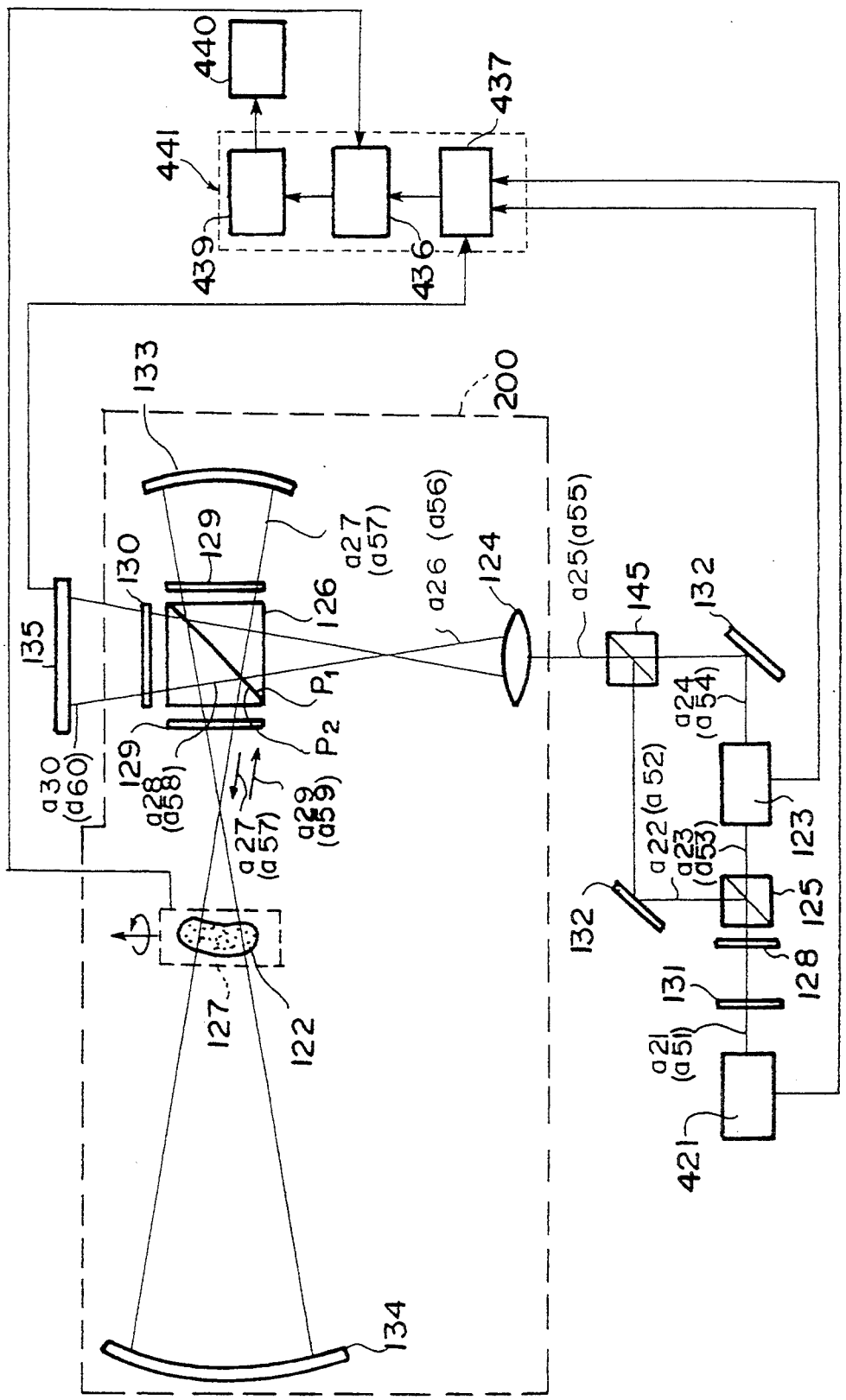
FIG. 14 is a block diagram showing a twelfth embodiment of the apparatus for obtaining three-dimensional information of a sample in accordance with the present invention.

FIG. 14 is a block diagram showing a twelfth embodiment of the apparatus for obtaining three-dimensional information of a sample in accordance with the present invention. In this embodiment, the polarization beam splitter 126, which is employed as the second optical path splitting means in the tenth embodiment of FIG. 12, also serves as the polarization beam splitter 138 acting as the second wavefront matching means. Also, the concave mirrors 133 and 134 serving as the reflection means are located at positions that cause the laser beam having passed through the sample 122 to travel to the polarization beam splitter 126 serving as the second optical path splitting means. Further, two quarter-wave plates 129, 129 are located which rotate the plane of polarization of the laser beam and which control the reflection or the passage of the laser beam at the polarization beam splitter 126. The other configurations are the same as those in the tenth embodiment of Figure 12.

How the twelfth embodiment operates will be described hereinbelow.

The laser beam a21 having the frequency ν0 is produced by the variable frequency laser beam source 421. The laser beam a21 is split by the halfwave plate 128 and the polarization beam splitter 125 into the laser beams a22 and a23 having the planes of polarization, which are normal to each other. The laser beam a23 is converted by the frequency shifter 123 into the laser beam a24 having the frequency ν0+Δν slightly different from the original frequency ν0.

The wave fronts of two laser beams a22 and a24 having the planes of polarization, which are normal to each other, and having the slightly different frequencies, are matched with each other by the second polarization beam splitter 145. The wavefront-matched laser beam a25 is thereby obtained. The wavefront-matched laser beam a25 is formed by the lens 124 into the laser beam a26 having the shape of a conical beam.

The laser beam a26 having been formed into the shape of the conical beam is split by the polarization beam splitter 126 into the laser beam a27 having the frequency ν0 and the laser beam a28 having the frequency ν0+Δν.

At this time, the laser beam a27 is reflected by a reflection surface P1 of the polarization beam splitter 126, and the laser beam a28 passes through the polarization beam splitter 126.

The laser beam a27 reflected by the reflection surface P1 of the polarization beam splitter 126 passes through the right quarter-wave plate 129, is reflected by the concave mirror 133 having a radius of curvature R, and again passes through the right quarter-wave plate 129. At this time, the laser beam a27 passes two times through the right quarter-wave plate 129. Therefore, the plane of polarization of the laser beam a27 is rotated 90°, and the laser beam a27 now passes through the reflection surface P1 of the polarization beam splitter 126.

The laser beam a27, which has thus passed through the polarization beam splitter 126, passes through the left quarter-wave plate 129 and is irradiated to the sample 122 such that it may impinge as a surface beam upon the sample 122. The laser beam, which has passed through the sample 122 and has been radiated out of the sample 122, is reflected by the concave mirror 134 having a radius of curvature 2R. The concave mirror 134 is located at the position facing the concave mirror 133 such that its center of curvature may coincide with the center of curvature of the concave mirror 133. The laser beam, which has been reflected by the concave mirror 134, again impinges upon the sample 122.

The laser beam, which has again impinged upon the sample 122, passes through the sample 122 and is radiated out of the sample 122 as a laser beam a29. The laser beam a29 again passes through the left quarter-wave plate 129. Therefore, the plane of polarization of the laser beam a29 is rotated 90°, and the laser beam a29 is then reflected by a reflection surface P2 of the polarization beam splitter 126. At this time, the wave front of the laser beam, which has passed through the sample 122 without being scattered and which is contained in the laser beam a29 radiated out of the sample 122, is matched with the wave front of the laser beam a28 having the frequency $v0+\Delta v$.

The effects that follow are the same as those in the tenth embodiment shown in FIG. 12.

In the twelfth embodiment, the sample 122 is irradiated to the laser beam two times, i.e. when the laser beam travels from the concave mirror 133 to the concave mirror 134 and when the laser beam is reflected by the concave mirror 134 and then travels from the concave mirror 134 to the polarization beam splitter 126. Therefore, the measurement means 439 is set such that these effects may be taken into consideration during the measurement operation.

An embodiment of the apparatus for obtaining three-dimensional information of a sample in accordance with the present invention, wherein the time required for the scanning is kept short, will be described hereinbelow.

Figure 15A:
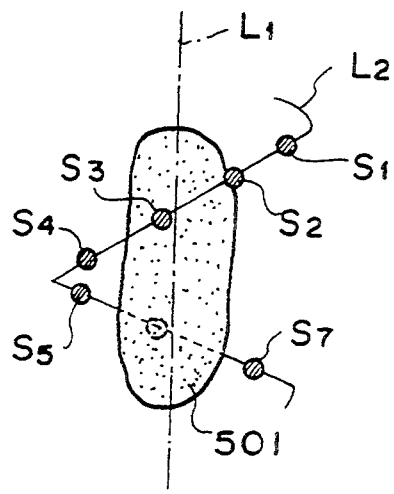
FIG. 15A is an explanatory view showing a thirteenth embodiment of the apparatus for obtaining three-dimensional information of a sample in accordance with the present invention.
Figure 15B:
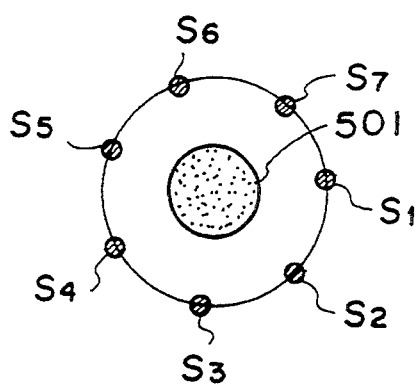
FIG. 15B is a plan view of FIG. 15A.
Figure 15C:
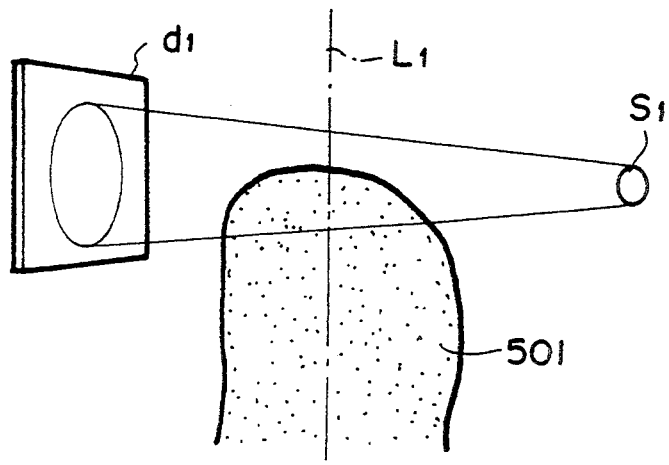
FIG. 15C is an enlarged view showing part of FIG. 15A.

FIGS. 15A, 15B, and 15C are explanatory views showing a thirteenth embodiment of the apparatus for obtaining three-dimensional information of a sample in accordance with the present invention. FIG. 15A shows seven laser beam irradiating means S1, S2, ..., S7, which are located in approximately equally spaced relation to one another on a helical path L2 having its center axis of rotation at a body axis L1 of a sample 501. FIG. 15B is a plan view of FIG. 15A, and FIG. 15C is an enlarged view showing part of FIG. 15A. A laser beam, which has been irradiated from the laser beam irradiating means S1, passes through the sample 501. As illustrated in FIG. 15C, a two-dimensional parallel operation type of image sensor d1 two-dimensionally detects the intensity of the laser beam, which has passed through the sample 501. Though not shown in FIG. 15A, the two-dimensional parallel operation type of image sensor is provided for each of the seven laser beam irradiating means S1, S2, ..., S7.

This embodiment will hereinbelow be described in detail with reference to FIG. 16.

This embodiment is provided with a laser beam source 502, which serves as an electromagnetic wave producing means, and an intensity correcting plate 503, with which the intensity distribution of the laser beam having been produced by the laser beam source 502 is made constant. This embodiment is also provided with a halfwave plate 504 and a polarization beam splitter 505 for splitting the laser beam into two laser beams, whose planes of polarization are normal to each other.

A frequency shifter 506 converts the frequency of one of the split laser beams into a slightly different frequency. This embodiment is further provided with a polarization beam splitter 507, which matches the wave fronts of the two laser beams with each other. These elements constitute a laser beam producing section 520.

The seven laser beam irradiating means S1, S2, ..., S7, which serve as a plurality of electromagnetic wave irradiating means, are located on a helical path around the sample 501. Each of the laser beam irradiating means S1, S2, ..., S7 is provided with a lens 508 for forming the laser beam into the shape of a conical beam, and a polarization beam splitter 509 which splits the laser beam into two laser beams and matches the wave fronts of the two laser beams with each other. Each of the laser beam irradiating means S1, S2, ..., S7 is also provided with quarter-wave plates 510, 510, each of which rotates the plane of polarization of the laser beam by an angle of 45°, and a first concave mirror 511 for reflecting one of the laser beams split by the polarization beam splitter 509. Each of the laser beam irradiating means S1, S2, ..., S7 is further provided with a second concave mirror 512, the center of curvature of which coincides with the center of curvature of the first concave mirror 511 and which reflects the laser beam having been reflected by the first concave mirror 511 and causes it to travel to the polarization beam splitter 509, and a polarizing plate 513.

Figure 16:
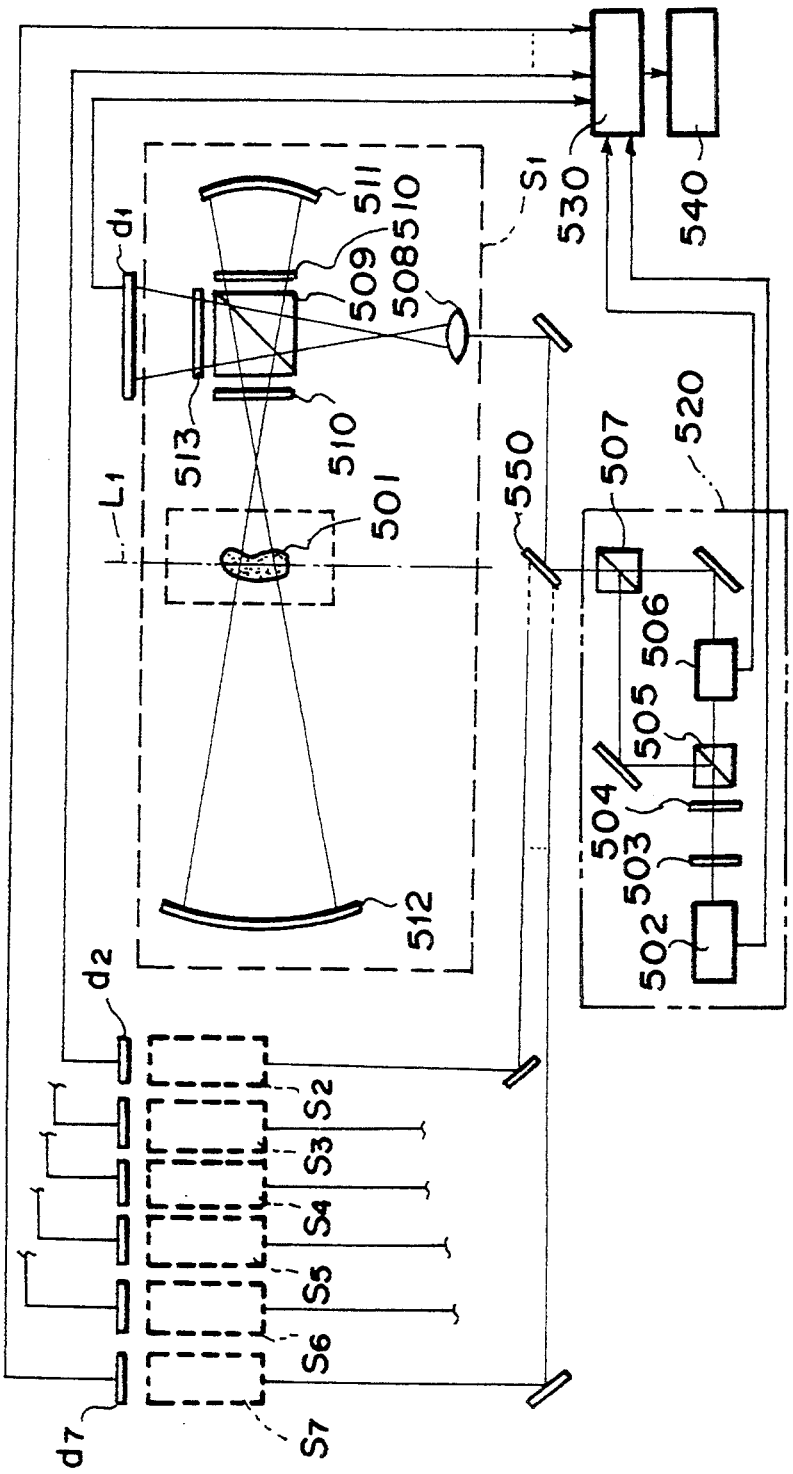
FIG. 16 is a block diagram showing the thirteenth embodiment of the apparatus for obtaining three-dimensional information of a sample in accordance with the present invention.

In FIG. 16, as an aid in facilitating the explanation, the internal structures of the laser beam irradiating means S2, S3, ..., S7 are not shown. All of the laser beam irradiating means S1, S2, ..., S7 have the same size and the same structure.

Seven two-dimensional parallel operation type of image sensors d1, d2, ..., d7 corresponding respectively to the seven laser beam irradiating means S1, S2, ..., S7 are located as the laser beam detecting means for two-dimensionally detecting the intensities of the laser beams having passed through the sample 501.

A measurement processing means 530 separately detects images of the sample 501 projected by the laser beams, which have passed through the sample 501, from the seven two-dimensional intensity distribution images, which have been detected by the image sensors d1, d2, ..., d7, by using the optical heterodyne detection technique. The measurement processing means 530 also obtains three-dimensional information of the sample 501 from the seven images of the sample 501, which are projected by the laser beams having passed through the sample 501 and which have been separately detected, by using the CT technique for the helical scanning. A reconstruction means 540 reconstructs a three-dimensional image of the sample 501, a tomographic image along an arbitrary cross-section in the sample 501, or the like, from the obtained three-dimensional information of the sample 501. A rotatable mirror 550 serves as a direction change-over means for sequentially guiding the laser beam, which has been produced by the laser beam producing means 520, to the seven laser beam irradiating means S1, S2, ..., S7. FIG. 17A is a perspective view showing the laser beam irradiating means S1, S2, ..., S7 and the two-dimensional parallel operation type of image sensors d1, d2, ..., d7, the view being taken along the direction of the body axis L1 of the sample 501.

FIG. 17B is a sectional view taken along line I—I of FIG. 17A. FIG. 17C is a sectional view taken along line II—II of FIG. 17A. FIG. 17D is a sectional view taken along line III—III of FIG. 17A.

How the thirteenth embodiment operates will be described hereinbelow.

The optical path of the laser beam, which has been produced by the laser beam source 502, is split into two optical paths by the polarization beam splitter 505. The laser beam, which travels along one of the two split optical paths, is converted by the frequency shifter 506 into a laser beam having a frequency slightly different from the original frequency. (The laser beam having the converted frequency will hereinbelow be referred to as the local oscillation laser beam.) The wave front of the local oscillation laser beam and the wave front of the laser beam (hereinafter referred to as the signal laser beam) traveling along the other optical path are matched with each other by the polarization beam splitter 507. The wavefront-matched laser beam, which has thus been obtained from the polarization beam splitter 507, is radiated out of the laser beam producing section 520.

The direction of the optical path of the laser beam having been radiated out of the laser beam producing section 520 is changed by the optical path change-over mirror 550. In this manner, the laser beam is guided to the laser beam irradiating means S1.

The laser beam impinging upon the laser beam irradiating means S1 is formed into the shape of a conical beam, and is then split by the polarization beam splitter 509 into the signal laser beam and the local oscillation laser beam. The signal laser beam impinges as a surface beam upon the sample 501. The wave front of the signal laser beam, which has passed through the sample 501, and the wave front of the local oscillation laser beam are matched with each other by the polarization beam splitter 509, and a wavefront-matched laser beam is thereby obtained. The two-dimensional intensity distribution image formed by the wavefront-matched laser beam is detected by the two-dimensional parallel operation type of image sensor (hereinafter referred to as the image sensor) d1.

Thereafter, the optical path change-over mirror 550 is rotated such that the laser beam having been produced by the laser beam producing section 520 may impinge upon the laser beam irradiating means S2. In this case, in the same manner as that when the laser beam impinged upon the laser beam irradiating means S1, the laser beam projects a two-dimensional intensity distribution image on the image sensor d2.

The optical path change-over mirror 550 is then rotated such that the laser beam having been produced by the laser beam producing section 520 may impinge upon the laser beam irradiating means S3. In the same manner as that described above, the laser beam projects a two-dimensional intensity distribution image on the image sensor d3.

In the manner described above, the mirror 550 is rotated, and the laser beam is sequentially caused to impinge upon the laser beam irradiating means S1, S2, ..., S7. The corresponding two-dimensional intensity distribution images are thereby detected.

Signals representing the seven two-dimensional intensity distribution images, which have been detected by the image sensors d1, d2, ..., d7, are fed into the measurement processing means 530. The measurement processing means 530 carries out a measurement processing operation on the signals, which represent the seven obtained two-dimensional intensity distribution images, by using the optical heterodyne detection technique, and converts them into images of the sample 501 projected by the laser beams, which have passed through the sample 501. The measurement processing means 530 also obtains three-dimensional information of the sample 501 from the seven images of the sample 501, which are projected by the laser beams having passed through the sample 501, by using the CT technique for the helical scanning. The reconstruction means 540 reconstructs a three-dimensional image of the sample 501, a tomographic image along an arbitrary cross-section in the sample 501, or the like, from the obtained three-dimensional information of the sample 501.

With the thirteenth embodiment described above, the laser beam irradiating means S1, S2, ..., S7, the image sensors d1, d2, ..., d7, and the sample 501 need not be moved. The images of the sample 501 projected by the laser beams having passed through the sample 501, which images have continuity with respect to the body axis of the sample 501, can be detected merely by slightly rotating the optical path change-over mirror 550. Also, the time required to scan the sample 550 or the laser beam irradiating means S1, S2, ..., S7 can be kept short.

The thirteenth embodiment may be modified in various other ways. For example, seven laser beam producing sections 520, 520, ... may be located for .the seven laser beam irradiating means S1, S2, ..., S7. In such cases, the optical path change-over mirror 550 need not be provided, and therefore the time required to rotate the optical path change-over mirror 550 can be eliminated.

The electromagnetic wave irradiated to the sample 501 need not necessarily be the laser beam, and may be near infrared rays, X-rays, or the like. For example, in cases where X-rays are employed as the electromagnetic wave, X-ray sources can be directly located at the positions of the electromagnetic wave irradiating means. Specifically, a plurality of X-ray sources may be located on a helical path around the sample 501, and means for detecting the X-rays, which have passed through the sample 501, may be located on extensions of lines connecting the X-ray sources and the sample 501.

What is claimed is:

1. A method for obtaining three-dimensional information of a sample, comprising the steps of:
   i) irradiating a laser beam, which has been formed into the shape of a conical beam, to a sample,
   ii) displacing the laser beam with respect to said sample such that the laser beam may helically scan said sample,
   iii) selecting the laser beam having passed through said sample to the same direction as the direction, along which the laser beam impinging upon said sample propagates conically, from the laser beam, which has scanned said sample and which has been radiated out of said sample, said selection being carried out by using an image forming lens and a pinhole,
   iv) detecting a two-dimensional intensity distribution of the laser beam, which has passed through said sample and which has been selected, and
   v) obtaining three-dimensional information representing the form and/or structure of said sample from said detected two-dimensional intensity distribution by using a computed tomography technique.

2. A method as defined in claim 1 wherein said sample is a living body.

3. An apparatus for obtaining three-dimensional information of a sample, comprising:
  i) a laser beam source,
  ii) an optical means for forming the laser beam, which has been produced by said laser beam source, into the shape of a conical beam,
  iii) a scanning means, which irradiates the laser beam formed into the shape of the conical beam to a sample such that the laser beam may impinge as a surface beam upon said sample, and which displaces the laser beam with respect to said sample such that the laser beam may helically scan said sample,
  iv) an optical direction selecting means, which condenses the laser beam having passed through said sample, and which allows a small spot formed by the condensed laser beam to pass therethrough,
  v) a two-dimensional intensity detecting means, which detects a two-dimensional intensity distribution of the laser beam selected by said optical direction selecting means, and
  vi) a measurement processing means, which carries out a measurement processing operation in order to obtain three-dimensional information representing the form and/or structure of said sample from the detected intensity distribution of the laser beam by using a computed tomography technique.

4. An apparatus as defined in claim 3 wherein said sample is a living body.

5. An apparatus as defined in claim 3 wherein said two-dimensional intensity detecting means is a two-dimensional parallel operation type of image sensor.

6. A method for obtaining three-dimensional information of a sample, comprising the steps of:
  i) irradiating a laser beam, which has been formed into the shape of a conical beam, to a sample,
  ii) displacing the laser beam with respect to said sample such that the laser beam may helically scan said sample,
  iii) matching a wave front of the laser beam, which has scanned said sample and has passed through said sample, with a wave front of a laser beam having a frequency slightly different from the frequency of the laser beam, which has scanned said sample and has passed through said sample, a wavefront-matched laser beam being thereby obtained,
  iv) two-dimensionally detecting the wavefront-matched laser beam with an optical heterodyne detection technique, a beat signal being thereby detected,
  v) measuring the intensity of the laser beam, which has passed through said sample, from said beat signal, and
  vi) obtaining three-dimensional information representing the form and/or structure of said sample from the intensity of the laser beam, which has passed through said sample, by using a computed tomography technique.

7. A method as defined in claim 6 wherein said sample is a living body.

8. A method for obtaining three-dimensional information of a sample, comprising the steps of:
  i) matching a wave front of a first laser beam with a wave front of a second laser beam having a frequency slightly different from the frequency of the first laser beam, a wavefront-matched laser beam being thereby obtained,
  ii) forming the wavefront-matched laser beam into the shape of a conical beam,
  iii) splitting an optical path of the laser beam, which has been formed into the shape of a conical beam, into an optical path of a laser beam, which has the same frequency as the frequency of the first laser beam, and an optical path of a laser beam, which has the same frequency as the frequency of the second laser beam,
  iv) irradiating either one of the two laser beams, which respectively travel along the two split optical paths, to a sample,
  v) displacing the laser beam, which is irradiated to said sample, with respect to said sample such that the laser beam may helically scan said sample,
  vi) matching a wave front of the laser beam, which has scanned said sample and has passed through said sample, with a wave front of the other laser beam obtained by splitting the optical path, a wavefront-matched laser beam being thereby obtained from the laser beam having scanned said sample and the other laser beam,
  vii) two-dimensionally detecting the wavefront-matched laser beam, which has thus been obtained from the laser beam having scanned said sample and the other laser beam, with an optical heterodyne detection technique, a beat signal being thereby detected,
  viii) measuring the intensity of the laser beam, which has passed through said sample, from said beat signal, and
  ix) obtaining three-dimensional information representing the form and/or structure of said sample from the intensity of the laser beam, which has passed through said sample, by using a computed tomography technique.

9. A method as defined in claim 8 wherein said sample is a living body.

10. An apparatus for obtaining three-dimensional information of a sample, comprising:
  i) a laser beam source for producing a laser beam having a single frequency,
  ii) an optical path splitting means, which is located in an optical path of the laser beam having been produced by said laser beam source and which splits the optical path of the laser beam into two optical paths,
  iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other,
  iv) optical means for forming the laser beams, which travel along the two split optical paths, respectively into the shapes of conical beams,
  v) a scanning means, which irradiates either one of the two laser beams formed into the shapes of the conical beams to a sample such that the laser beam may impinge as a surface beam upon said sample, and which displaces the laser beam with respect to said sample such that the laser beam may helically scan said sample,
  vi) a wavefront matching means for matching a wave front of the laser beam, which has been irradiated to said sample and has passed through said sample, with a wave front of the other laser beam formed into the shape of the conical beam, a wavefront-matched laser beam being thereby obtained, vii) a two-dimensional intensity detecting means, which is located in a plane intersecting approximately perpendicularly to the direction of travel of the wavefront-matched laser beam obtained from said wavefront matching means, and which two-dimensionally detects the optical intensity repeatedly becoming high and low at a frequency equal to the difference between the frequencies of the laser beams subjected to the wavefront matching, and viii) a measurement processing means, which detects the intensity of the laser beam having passed through said sample from the laser beam intensity detected by said two-dimensional intensity detecting means, and which carries out a measurement processing operation in order to obtain three-dimensional information representing the form and/or structure of said sample by using a computed tomography technique.

11. An apparatus as defined in claim 10 wherein said sample is a living body.

12. An apparatus as defined in claim 10 wherein said two-dimensional intensity detecting means is a two-dimensional parallel operation type of image sensor.

13. An apparatus for obtaining three-dimensional information of a sample, comprising:

i) a laser beam source for producing a laser beam having a single frequency, ii) a first optical path splitting means, which is located in an optical path of the laser beam having been produced by said laser beam source and which splits the optical path of the laser beam produced by said laser beam source into a first laser beam traveling along a first optical path and a second laser beam traveling along a second optical path, iii) a frequency converting means, which converts the frequency of at least one of said first and second laser beams respectively traveling along the first and second optical paths into a different frequency such that the frequency of the first laser beam traveling along the first optical path and the frequency of the second laser beam traveling along the second optical path may become slightly different from each other, iv) a first wavefront matching means for matching a wave front of the laser beam, the frequency of which has been converted, with a wave front of the laser beam which travels along one of the first and second optical paths, a wavefront-matched laser beam being thereby obtained, v) an optical means for forming the wavefront-matched laser beam, which has been obtained from said first wavefront matching means, into the shape of a conical beam, vi) a second optical path splitting means for splitting the optical path of the laser beam, which has been formed into the shape of the conical beam, into a third optical path of a third laser beam formed from one of the first and second laser beams having slightly different frequencies and a fourth optical path of a fourth laser beam formed from the other of the first and second laser beams, vii) a scanning means, which irradiates one of the third and fourth laser beams to a sample such that the laser beam may impinge as a surface beam upon said sample, and which displaces said one of the third and fourth laser beams with respect to said sample such that said one of the third and fourth laser beams may helically scan said sample, viii) a second wavefront matching means for matching a wave front of the laser beam, which has been irradiated to said sample and has passed through said sample, with a wave front of the laser beam traveling along the other of the third and fourth optical paths split by said second optical path splitting means, a wavefront-matched laser beam being thereby obtained, ix) a two-dimensional intensity detecting means, which is located in a plane intersecting approximately perpendicularly to the direction of travel of the wavefront-matched laser beam obtained from said second wavefront matching means, and which two-dimensionally detects the optical intensity repeatedly becoming high and low at a frequency equal to the difference between the frequencies of the laser beams subjected to the wavefront matching in said second wavefront matching means, and x) a measurement processing means, which detects the intensity of the laser beam having passed through said sample from the laser beam intensity detected by said two-dimensional intensity detecting means, and which carries out a measurement processing operation in order to obtain three-dimensional information of said sample by using a computed tomography technique.

14. An apparatus as defined in claim 13 wherein said second optical path splitting means also serves as said second wavefront matching means, and a reflection means is provided which is located at a position such that the laser beam having passed through said sample may be caused to travel to said second optical path splitting means.

15. An apparatus as defined in claim 13 wherein said sample is a living body.

16. An apparatus as defined in claim 13 wherein said two-dimensional intensity detecting means is a two-dimensional parallel operation type of image sensor.

17. A method for obtaining three-dimensional information of a sample, comprising the steps of:

i) carrying out a measurement operation on each of at least two laser beams having different frequencies, said measurement operation comprising the steps of:

a) forming a laser beam, which has a certain frequency, into the shape of a conical beam, b) irradiating the laser beam, which has been formed into the shape of the conical beam, to a sample, c) displacing the laser beam with respect to said sample such that the laser beam may helically scan said sample, d) selecting the laser beam having passed through said sample to the same direction as the direction, along which the laser beam impinging upon said sample propagates conically, from the laser beam, which has scanned said sample and which has been radiated out of said sample, said selection being carried out by using an image forming lens and a pinhole, and e) detecting a two-dimensional intensity distribution of the laser beam, which has passed through said sample and which has been selected, and ii) obtaining three-dimensional information representing constituents and/or functions of said sample from the two-dimensional intensity distributions of at least two of the selected laser beams having different frequencies, which distributions have been detected by the measurement operations, by using a computed tomography technique.

18. A method as defined in claim 17 wherein said sample is a living body.

19. An apparatus for obtaining three-dimensional information of a sample, comprising:
   i) a laser beam source capable of producing at least two laser beams having different frequencies,
   ii) an optical means for forming a laser beam, which has been produced by said laser beam source, into the shape of a conical beam,
   iii) a scanning means, which irradiates the laser beam formed into the shape of the conical beam to a sample such that the laser beam may impinge as a surface beam upon said sample, and which displaces the laser beam with respect to said sample such that the laser beam may helically scan said sample,
   iv) an optical direction selecting means for selecting laser beams, by condensing the laser beam having passed through said sample, and for allowing a small spot formed by the condensed laser beam to pass therethrough,
   v) a two-dimensional intensity detecting means, which detects a two-dimensional intensity distribution of the laser beam selected by said optical direction selecting means, said two-dimensional intensity distribution being projected from said small spot, and
   vi) a measurement processing means, which calculates values concerning constituents and/or functions of said sample from the two-dimensional intensity distributions of at least two of the selected laser beams having different frequencies, said two-dimensional intensity distributions being obtained when at least two laser beams are respectively irradiated to said sample, and which thereby obtains three-dimensional information representing constituents and/or functions of said sample.

20. An apparatus as defined in claim 19 wherein said sample is a living body.

21. An apparatus as defined in claim 19 wherein said two-dimensional intensity detecting means is a two-dimensional parallel operation type of image sensor.

22. A method for obtaining three-dimensional information of a sample, comprising the steps of:
   i) carrying out a measurement operation on each of at least two laser beams having different frequencies, said measurement operation comprising the steps of:
      a) forming a laser beam, which has a certain frequency, into the shape of a conical beam,
      b) irradiating the laser beam, which has been formed into the shape of the conical beam, to a sample,
      c) displacing the laser beam with respect to said sample such that the laser beam may helically scan said sample,
      d) matching a wave front of the laser beam, which has scanned said sample and has passed through said sample, with a wave front of a laser beam having a frequency slightly different from the frequency of the laser beam, which has scanned said sample and has passed through said sample, a wavefront-matched laser beam being thereby obtained,
      e) two-dimensionally detecting the wavefront-matched laser beam with an optical heterodyne detection technique, a beat signal being thereby detected, and
      f) measuring the intensity of the laser beam, which has passed through said sample, from said beat signal, and
   ii) obtaining three-dimensional information representing constituents and/or functions of said sample from two-dimensional intensity distributions for at least two of the laser beams which have scanned said sample and have passed through said sample having different frequencies, which distributions have been detected by the measurement operations, by using a computed tomography technique.

23. A method as defined in claim 22 wherein said sample is a living body.

24. An apparatus for obtaining three-dimensional information of a sample, comprising:
   i) a laser beam source capable of producing at least two laser beams having different frequencies,
   ii) an optical path splitting means, which is located in an optical path of a laser beam having been produced by said laser beam source and which splits the optical path of the laser beam into two optical paths,
   iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other,
   iv) optical means for forming the laser beams, which travel along the two split optical paths, respectively into the shapes of conical bemas,
   v) a scanning means, which irradiates either one of the two laser beams formed into the shapes of the conical beams to a sample such that the laser beam may impinge as a surface beam upon said sample, and which displaces the laser beam with respect to said sample such that the laser beam may helically scan said sample,
   vi) a wavefront matching means for matching a wave front of the laser beam, which has been irradiated to said sample and has passed through said sample, with a wave front of the other laser beam formed into the shape of the conical beam, a wavefront-matched laser beam being thereby obtained;
   vii) a two-dimensional intensity detecting means, which is located in a plane intersecting approximately perpendicularly to the direction of travel of the wavefront-matched laser beam obtained from said wavefront matching means, and which two-dimensionally detects the optical intensity repeatedly becoming high and low at a frequency equal to the difference between the frequencies of the laser beams subjected to the wavefront matching, and
   viii) a measurement processing means, which detects the intensity of the laser beam having passed through said sample from the laser beam intensity detected by said two-dimensional intensity detecting means, and which calculates values concerning constituents and/or functions of said sample from two-dimensional intensity distributions of at least two of the laser beams having passed through said sample having different frequencies, said dimensional intensity distributions being obtained when at least two laser beams are respectively irradiated to said sample, said measurement processing means thereby obtaining three-dimensional information representing constituents and/or functions of said sample by using a computed tomography technique.

25. An apparatus as defined in claim 24 wherein said sample is a living body.

26. An apparatus as defined in claim 24 wherein said two-dimensional intensity detecting means is a two-dimensional parallel operation type of image sensor.

27. An apparatus for obtaining three-dimensional information of a sample, comprising:
 i) a laser beam source capable of producing at least two laser beams having different frequencies,
 ii) a first optical path splitting means, which is located in an optical path of a laser beam having been produced by said laser beam source and which splits the optical path of the laser beam into two optical paths,
 iii) a frequency converting means, which converts the frequency of at least either one of laser beams respectively traveling along the two split optical paths into a different frequency such that the frequency of the laser beam traveling along one of the two split optical paths and the frequency of the laser beam traveling along the other optical path may become slightly different from each other,
 iv) a first wavefront matching means for matching a wave front of the laser beam, the frequency of which has been converted, with a wave front of the laser beam, which travels along one of the two split optical paths, a wavefront-matched laser beam being thereby obtained,
 v) an optical means for forming the wavefront-matched laser beam, which has been obtained from said first wavefront matching means, into the shape of a conical beam,
 vi) a second optical path splitting means for splitting the optical path of the laser beam, which has been formed into the shape of the conical beam, into an optical path of one of the two laser beams having slightly different frequencies and an optical path of the other laser beam,
 vii) a scanning means, which irradiates the laser beam, that travels along either one of the two optical paths split by said second optical path splitting means, to a sample such that the laser beam may impinge as a surface beam upon said sample, and which displaces the laser beam with respect to said sample such that the laser beam may helically scan said sample,
 viii) a second wavefront matching means for matching a wave front of the laser beam, which has been irradiated to said sample and has passed through said sample, with a wave front of the laser beam traveling along the other of the two optical paths split by said second optical path splitting means, a wavefront-matched laser beam being thereby obtained,
 ix) a two-dimensional intensity detecting means, which is located in a plane intersecting approximately perpendicularly to the direction of travel of the wavefront-matched laser beam obtained from said second wavefront matching means, and which two-dimensionally detects the optical intensity repeatedly becoming high and low at a frequency equal to the difference between the frequencies of the laser beams subjected to the wavefront matching in said second wavefront matching means, and
 x) a measurement processing means, which detects the intensity of the laser beam having passed through said sample from the laser beam intensity detected by said two-dimensional intensity detecting means, and which calculates values concerning constituents and/or functions of said sample from two-dimensional intensity distributions of at least two laser beams having different frequencies, said two-dimensional intensity distributions being obtained when at least two laser beams are respectively irradiated to said sample, said measurement processing means thereby obtaining three-dimensional information representing constituents and/or functions of said sample by using a computed tomography technique.

28. An apparatus as defined in claim 27 wherein said second optical path splitting means also serves as said second wavefront matching means, and a reflection means is provided which is located at a position such that the laser beam having passed through said sample may be caused to travel to said second optical path splitting means.

29. An apparatus as defined in claim 27 wherein said sample is a living body.

30. An apparatus as defined in claim 27 wherein said two-dimensional intensity detecting means is a two-dimensional parallel operation type of image sensor.

31. A method for obtaining three-dimensional information of a sample, wherein a beam of an electromagnetic wave is irradiated to a sample, the beam of the electromagnetic wave is displaced with respect to said sample such that the beam of the electromagnetic wave may helically scan said sample, the intensity of the beam of the electromagnetic wave having passed through said sample is detected, and three-dimensional information of said sample is obtained from the detected intensity of the beam of the electromagnetic wave,
 the method for obtaining three-dimensional information of a sample comprising the steps of:
 i) irradiating a plurality of beams of the electromagnetic wave from a plurality of electromagnetic wave irradiating means to said sample, the plurality of said electromagnetic wave irradiating means being located in equally spaced relation to one another around said sample such that they helically surround said sample at least over 360 degrees around said sample, and
 ii) detecting intensities of the plurality of the beams of the electromagnetic wave, which have passed through said sample, by using a plurality of electromagnetic wave detecting means, each of which is located at a position that is capable of detecting one of the beams of the electromagnetic wave having passed through said sample.

32. A method as defined in claim 31 wherein the plurality of the beams of the electromagnetic wave are irradiated to said sample by sequentially causing a beam of the electromagnetic wave, which has been produced by a single electromagnetic wave producing means, to impinge upon the plurality of said electromagnetic wave irradiating means.

33. A method as defined in claim 31 wherein said sample is a living body.

34. A method as defined in claim 31 wherein said electromagnetic wave is a laser beam.

35. An apparatus for obtaining three-dimensional information of a sample, wherein a beam of an electromagnetic wave is irradiated to a sample, the beam of the electromagnetic wave is displaced with respect to said sample such that the beam of the electromagnetic wave may helically scan said sample, the intensity of the beam of the electromagnetic wave having passed through said sample is detected, and three-dimensional information of said sample is obtained from the detected intensity of the beam of the electromagnetic wave, the apparatus for obtaining three-dimensional information of a sample comprising:
i) at least a single electromagnetic wave producing means,
ii) a plurality of electromagnetic wave irradiating means, which are located in equally spaced relation to one another around said sample such that they helically surround said sample at least over 360 degrees around said sample, and each of which receives a beam of the electromagnetic wave having been produced by said electromagnetic wave producing means and irradiates the beam of the electromagnetic wave to said sample, and
iii) a plurality of electromagnetic wave detecting means, each of which detects the intensity of one of the beams of the electromagnetic wave having passed through said sample.

36. An apparatus as defined in claim 35 wherein only a single electromagnetic wave producing means is provided, and a direction change-over means is provided which sequentially changes over the direction of travel of the beam of the electromagnetic wave having been produced by said electromagnetic wave producing means such that the beam of the electromagnetic wave may travel toward each of the plurality of said electromagnetic wave irradiating means.

37. An apparatus as defined in claim 35 wherein said sample is a living body.

38. An apparatus as defined in claim 35 wherein said electromagnetic wave is a laser beam.

* * * * *